US008946175B1

(12) United States Patent
Kandimalla et al.

(10) Patent No.: US 8,946,175 B1
(45) Date of Patent: *Feb. 3, 2015

(54) STABILIZED IMMUNOMODULATORY OLIGONUCLEOTIDES

(75) Inventors: Ekambar R. Kandimalla, Hopkinton, MA (US); Lakshmi Bhagat, Framingham, MA (US); Rajendra K. Pandey, Framingham, MA (US); Dong Yu, Westboro, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 487 days.

This patent is subject to a terminal disclaimer.

(21) Appl. No.: 13/210,903

(22) Filed: Aug. 16, 2011

Related U.S. Application Data

(63) Continuation of application No. 10/865,245, filed on Jun. 10, 2004, now Pat. No. 8,008,267.

(60) Provisional application No. 60/477,608, filed on Jun. 11, 2003, provisional application No. 60/499,038, filed on Aug. 29, 2003, provisional application No. 60/504,279, filed on Sep. 18, 2003.

(51) Int. Cl.
| | |
|---|---|
| *A61K 48/00* | (2006.01) |
| *A61K 45/00* | (2006.01) |
| *A61K 47/00* | (2006.01) |
| *A61K 39/00* | (2006.01) |
| *A61K 39/38* | (2006.01) |

(52) U.S. Cl.
USPC .................... 514/44 R; 424/184.1; 424/278.1

(58) Field of Classification Search
CPC .......... A61K 2039/55561; A61K 2039/55566; A61K 2039/60; A61K 2039/6025; C12N 15/117; C12N 2310/321; C12N 2310/3521
See application file for complete search history.

(56) References Cited

U.S. PATENT DOCUMENTS

| | | | |
|---|---|---|---|
| 5,366,878 A | 11/1994 | Pederson et al. | |
| 5,635,377 A | 6/1997 | Pederson et al. | |
| 5,652,355 A | 7/1997 | Metelev et al. | |
| 5,921,332 A | 7/1999 | Spedale, Jr. | |
| 6,143,881 A | 11/2000 | Metelev et al. | |
| 6,346,614 B1 | 2/2002 | Metelev et al. | |
| 8,003,619 B2 * | 8/2011 | Hartmann et al. | 514/44 A |
| 8,008,267 B2 * | 8/2011 | Kandimalla et al. | 514/44 R |
| 8,030,462 B2 * | 10/2011 | Kandimalla et al. | 536/23.1 |
| 8,106,173 B2 * | 1/2012 | Kandimalla et al. | 536/23.1 |
| 8,153,608 B2 * | 4/2012 | Agrawal et al. | 514/44 A |
| 8,153,777 B2 * | 4/2012 | Kandimalla et al. | 536/24.5 |
| 8,188,261 B2 * | 5/2012 | Kandimalla et al. | 536/24.5 |
| 8,202,850 B2 * | 6/2012 | Agrawal et al. | 514/44 R |
| 8,202,974 B2 * | 6/2012 | Lan et al. | 536/23.1 |
| 8,349,812 B2 * | 1/2013 | Debelak et al. | 514/52 |
| 8,357,665 B2 * | 1/2013 | Kandimalla et al. | 514/44 R |
| 8,361,986 B2 * | 1/2013 | Kandimalla et al. | 514/44 R |
| 8,362,233 B2 * | 1/2013 | Kandimalla et al. | 536/24.5 |
| 8,372,413 B2 * | 2/2013 | Fearon et al. | 424/278.1 |
| 8,377,898 B2 * | 2/2013 | Kandimalla et al. | 514/44 R |
| 8,383,598 B2 * | 2/2013 | Kandimalla et al. | 514/44 R |
| 8,399,423 B2 * | 3/2013 | Kandimalla et al. | 514/44 R |
| 8,420,615 B2 * | 4/2013 | Agrawal et al. | 514/44 R |
| 8,426,375 B2 * | 4/2013 | Kandimalla et al. | 514/44 R |
| 8,476,416 B2 * | 7/2013 | Kandimalla et al. | 536/23.1 |
| 8,486,908 B2 * | 7/2013 | Kandimalla et al. | 514/44 R |
| 8,492,358 B2 * | 7/2013 | Kandimalla et al. | 514/44 A |
| 8,716,253 B2 * | 5/2014 | Kandimalla et al. | 514/44 R |
| 8,759,310 B2 * | 6/2014 | Kandimalla et al. | 514/44 R |
| 2004/0097719 A1 * | 5/2004 | Agrawal et al. | 536/23.2 |
| 2005/0026861 A1 | 2/2005 | Kandimalla et al. | |

FOREIGN PATENT DOCUMENTS

| | | | |
|---|---|---|---|
| EP | 1393745 A1 | 3/2004 | |
| WO | WO01/51500 A1 | 7/2001 | |

OTHER PUBLICATIONS

Yu et al Nucleic Acids Research 2002 vol. 30 No. 20 pp. 4460-4469.*
Tokunaga et al., J. Nat. Can. Inst., 72(4):955-962 (1984).
Kataoka et al., Jpn. J. Can. Res. 83:244-247 (1992).
Hartmann et al., Ep. Journal of Imm., 33:1633-1641 (2003).
Marshall et al., Journal of Leukocyte Bio. 73:781-792 (2003).
Sato et al., Science 273:352-354 (1996).
Gurunathan et al., Ann. Rev. Imm. 18:927-974 (2000).
Pisetsky et al., Mol. Biol. Rep. 18:217-221 (1993).
Krieg et al., Nature 374:546-549 (1995).
Kandimalla et al., Curr. Opin. Mol. Ther. 4(2):122-129 (2002).
Agrawal et al., Current Cancer Drug Targets, 1:197-209 (2001).
Yu et al., Bioorg. Med. Chem. 9:2803-2808 (2001).
Yu et al., Bioorg. Med. Chem. Lett. 11:2263-2267 (2001).
Yu et al., Bioorg. Med. Chem. 11:459-464 (2003).
Yu et al., Bioorg. Med. Chem. Lett. 10:2585-2588 (2000).
Yu et al., Nuc. Acids Res. 30(20):4460-4469 (2002).
Yu et al., Biochem. Biophys. Res. Commun. 297:83-90 (2002).
Bhagat et al., Biochem. Biophys. Res. Commun. 300:853-861 (2003).
Kandimalla et al., Nuc. Acids Res. 31(9):2393-2400 (2003).
Kandimalla et al., Bioconj. Chem. 13:966-974 (2002).

(Continued)

*Primary Examiner* — Nita M Minnifield
(74) *Attorney, Agent, or Firm* — Elmore Patent Law Group, P.C.; Joseph C. Zucchero; Carolyn S. Elmore, Esq.

(57) ABSTRACT

The invention provides immunostimulatory oligonucleotides having at least one CpG dinucleotide and a secondary structure at the 5'- or 3'-end. These oligonucleotides have either reduced or improved immunostimulatory properties. The invention establishes that 5'-terminal secondary structures affect immunostimulatory activity significantly more than those at the 3'-end. The invention also provides methods for increasing or decreasing the immunostimulatory activity of a CpG-containing nucleic acid.

25 Claims, 16 Drawing Sheets

(56) References Cited

OTHER PUBLICATIONS

Remington's Pharm. Sci, 18$^{th}$ Ed, ed. Gennaro, Mack Pub. Co., PA, (1990) ISBN:0-912734-04-03.
Burgstaller et al., Curr. Opin. Drug. Disc. Devel. 5(5):690-700 (2002).
Iyer et al., J. Am. Chem. Soc. 112:1253-1254 (1990).
Hirao et al., Nuc. Acids Res. 22(4):576-582 (1994).
Zhao et al., Biochem. Pharmacol. 51:173-182 (1996).
Branda et al., Biochem. Pharmacol. 45(10):2037-2043 (1993).
Krug et al., Eur. J. Immunol. 31:2154-2163 (2001).
Hemmi et al., Nature 408:740-745 (2000).
Yi et al., J. Immunol. 161:4493-4497 (1998).
Stacey et al., J. Immunol. 157:2116-2122 (1996).

\* cited by examiner

Linkers for linear synthesis

SEQUENCE LISTING

<160> NUMBER OF SEQ ID NOS: 76

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(17)
<223> OTHER INFORMATION: phosphorothioate

<400> SEQUENCE: 1
ctgtctgacg ttctctg                                                    17

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate

<400> SEQUENCE: 2
ctgtctgacg ttctctggaa cagag                                           25

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<221> NAME/KEY: misc_feature
<222> LOCATION: (1)..(31)
<223> OTHER INFORMATION: phosphorothioate

<400> SEQUENCE: 3
ctgtctgacg ttctctggaa cagagaacgt c                              31

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate

<400> SEQUENCE: 4
ctgtctgacg ttctctggaa cagagaacgt cagacag                        37

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate

<400> SEQUENCE: 5
gacaggaact gtctgacgtt ctctg                                     25

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(32)
<223> OTHER INFORMATION: phosphorothioate

<400> SEQUENCE: 6
aacgtcagac aggaactgtc tgacgttctc tg                             32

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate

<400> SEQUENCE: 7
cagagaacgt cagacaggaa ctgtctgacg ttctctg                        37

<210> SEQ ID NO 8
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate

<400> SEQUENCE: 8
ctatctgacg ttctctgt                                                18

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate
<220> FEATURE:
<221> NAME/KEY: misc_feature
<222> LOCATION: (19)..(26)
<223> OTHER INFORMATION: phosphodiester

<400> SEQUENCE: 9
ctatctgacg ttctctgtgt gatcac                                       26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphodiester
<220> FEATURE:
<221> NAME/KEY: misc_feature
<222> LOCATION: (9)..(26)
<223> OTHER INFORMATION: phosphorothioate

<400> SEQUENCE: 10
gtgatcacct atctgacgtt ctctgt                                       26

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(17)
<223> OTHER INFORMATION: phosphorothioate

<400> SEQUENCE: 11
ctgtctgtcg ttctctg                                                 17

<210> SEQ ID NO 12
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate

<400> SEQUENCE: 12
ctgtctgtcg ttctctggaa cagag                                            25

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: phosphorothioate

<400> SEQUENCE: 13
ctgtctgtcg ttctctggaa cagagaacga c                                     31

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate

<400> SEQUENCE: 14
ctgtctgtcg ttctctggaa cagagaacga cagacag                               37

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate

<400> SEQUENCE: 15
gacaggaact gtctgtcgtt ctctg                                            25

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(32)
<223> OTHER INFORMATION: phosphorothioate

<400> SEQUENCE: 16
aacgacagac aggaactgtc tgacgttctc tg                                    32
```

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate

<400> SEQUENCE: 17
cagagaacga cagacaggaa ctgtctgtcg ttctctg                              37

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate

<400> SEQUENCE: 18
tcgtcgttga gctctgaaag agctc                                          25

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothioate

<400> SEQUENCE: 19
tcgtcgttgt gagctctgtg aaacagagct cac                                 33

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(41)
<223> OTHER INFORMATION: phosphorothioate

<400> SEQUENCE: 20
tcgtcgttgc acagagctct gctgaaagca gagctctgtg c                        41

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature

```
<222> LOCATION: (1)..(49)
<223> OTHER INFORMATION: phosphorothioate

<400> SEQUENCE: 21
tcgtcgttgc tgacagagct ctgctatgaa atagcagagc tctgtcagc        49

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate

<400> SEQUENCE: 22
tcgtcgttgt gctctgaact tgctc                                  25

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothioate

<400> SEQUENCE: 23
tcgtcgttgt gtgctctgtg aacatcagtc tac                         33

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate
<220> FEATURE:
<221> NAME/KEY: misc_feature
<222> LOCATION: (9)..(15)
<223> OTHER INFORMATION: phosphodiester
<220> FEATURE:
<221> NAME/KEY: misc_feature
<222> LOCATION: (16)..(18)
<223> OTHER INFORMATION: phosphorothioate
<220> FEATURE:
<221> NAME/KEY: misc_feature
<222> LOCATION: (19)..(25)
<223> OTHER INFORMATION: phosphodiester

<400> SEQUENCE: 24
tcgtcgttga gctctgaaag agctc                                  25

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (1)..(8)
<223> OTHER INFORMATION: phosphorothioate
<220> FEATURE:
<221> NAME/KEY: misc_feature
<222> LOCATION: (9)..(19)
<223> OTHER INFORMATION: phosphodiester
<220> FEATURE:
<221> NAME/KEY: misc_feature
<222> LOCATION: (20)..(22)
<223> OTHER INFORMATION: phosphorothioate
<220> FEATURE:
<221> NAME/KEY: misc_feature
<222> LOCATION: (23)..(33)
<223> OTHER INFORMATION: phosphodiester

<400> SEQUENCE: 25
tcgtcgttgt gagctctgtg aaacagagct cac                                33

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate
<220> FEATURE:
<221> NAME/KEY: modified_base
<222> LOCATION: (16)..(25)
<223> OTHER INFORMATION: 2'-O-methyl-ribonucleotide

<400> SEQUENCE: 26
tcgtcgttga gctctgaaag agctc                                         25

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothioate
<220> FEATURE:
<221> NAME/KEY: modified_base
<222> LOCATION: (20)..(33)
<223> OTHER INFORMATION: 2'-O-methyl-ribonucleotide

<400> SEQUENCE: 27
tcgtcgttgt gagctctgtg aaacagagct cac                                33

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate
<220> FEATURE:
<221> NAME/KEY: modified_base
<222> LOCATION: (3)
<223> OTHER INFORMATION: 2'-deoxy-7-deaza-G
<220> FEATURE:
```

```
<221> NAME/KEY: modified_base
<222> LOCATION: (6)
<223> OTHER INFORMATION: 2'-deoxy-7-deaza-G

<400> SEQUENCE: 28
tcgtcgttga gctctgaaag agctc                                          25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate
<220> FEATURE:
<221> NAME/KEY: modified_base
<222> LOCATION: (3)
<223> OTHER INFORMATION: araG
<220> FEATURE:
<221> NAME/KEY: modified_base
<222> LOCATION: (6)
<223> OTHER INFORMATION: araG

<400> SEQUENCE: 29
tcgtcgttga gctctgaaag agctc                                          25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate

<400> SEQUENCE: 30
tgctgcttga gctctgaaag agctc                                          25

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphorothioate

<400> SEQUENCE: 31
tcttgacgtt ctctct                                                    16

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate
```

```
<400> SEQUENCE: 32
tcttgacgtt ctctctgaaa gagag                                              25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: phosphorothioate
<220> FEATURE:
<221> NAME/KEY: misc_feature
<222> LOCATION: (20)..(25)
<223> OTHER INFORMATION: phosphodiester

<400> SEQUENCE: 33
tcttgacgtt ctctctgaaa gagag                                              25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphodiester
<220> FEATURE:
<221> NAME/KEY: misc_feature
<222> LOCATION: (17)..(25)
<223> OTHER INFORMATION: phosphorothioate

<400> SEQUENCE: 34
tcttgacgtt ctctctgaaa gagag                                              25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphodiester
<220> FEATURE:
<221> NAME/KEY: misc_feature
<222> LOCATION: (17)..(19)
<223> OTHER INFORMATION: phosphorothioate
<220> FEATURE:
<221> NAME/KEY: misc_feature
<222> LOCATION: (20)..(25)
<223> OTHER INFORMATION: phosphodiester

<400> SEQUENCE: 35
tcttgacgtt ctctctgaaa gagag                                              25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: misc_feature
<222> LOCATION: (1)..(25)
<223> OTHER INFORMATION: phosphodiester

<400> SEQUENCE: 36
tcttgacgtt ctctctgaaa gagag                                              25

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphorothioate

<400> SEQUENCE: 37
tcttgacgtt ctctct                                                        16

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphodiester

<400> SEQUENCE: 38
tcttgacgtt ctctct                                                        16

<210> SEQ ID NO 39
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate

<400> SEQUENCE: 39 tcgtcgtt                                                                  8

<210> SEQ ID NO 40
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate
<220> FEATURE:
<221> NAME/KEY: modified_base
<222> LOCATION: (3)
<223> OTHER INFORMATION: 2'-deoxy-7-deaza-G
<220> FEATURE:
<221> NAME/KEY: modified_base
```

```
<222> LOCATION: (6)
<223> OTHER INFORMATION: 2'-deoxy-7-deaza-G

<400> SEQUENCE: 40 tcgtcgtt                                                                 8

<210> SEQ ID NO 41
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate

<400> SEQUENCE: 41 ttgtgctt                                                                 8

<210> SEQ ID NO 42
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphorothioate

<400> SEQUENCE: 42 tcgtcgttg                                                                9

<210> SEQ ID NO 43
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphodiester

<400> SEQUENCE: 43 tcgtcgttg                                                                9

<210> SEQ ID NO 44
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphodiester

<400> SEQUENCE: 44 tcgtcgtt                                                                 8

<210> SEQ ID NO 45
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphorothioate
<220> FEATURE:
<221> NAME/KEY: misc_feature
<222> LOCATION: (10)..(21)
<223> OTHER INFORMATION: phosphodiester

<400> SEQUENCE: 45
tcgtcgttgt gcatcgatgc a                                             21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphodiester
<220> FEATURE:
<221> NAME/KEY: misc_feature
<222> LOCATION: (10)..(21)
<223> OTHER INFORMATION: phosphorothioate

<400> SEQUENCE: 46
tcgtcgttgt gcatcgatgc a                                             21

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothioate

<400> SEQUENCE: 47
cagagctctg                                                          10

<210> SEQ ID NO 48
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothioate
<220> FEATURE:
<221> NAME/KEY: modified_base
<222> LOCATION: (1)..(10)
<223> OTHER INFORMATION: 2'-O-methylribonucleotide

<400> SEQUENCE: 48
cagagcucug                                                          10

<210> SEQ ID NO 49
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothioate

<400> SEQUENCE: 49
cacacctctg                                                            10

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (3)..(12)
<223> OTHER INFORMATION: phosphodiester

<400> SEQUENCE: 50
ggcatcgatg cc                                                         12

<210> SEQ ID NO 51
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: phosphodiester

<400> SEQUENCE: 51 gagctc                                                                 6

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: phosphodiester

<400> SEQUENCE: 52
gacagagctc tgtc                                                       14

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (1)..(20)
<223> OTHER INFORMATION: phosphodiester

<400> SEQUENCE: 53
gctgacagag ctctgtcagc                                               20

<210> SEQ ID NO 54
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphodiester
<220> FEATURE:
<221> NAME/KEY: modified_base
<222> LOCATION: (1)..(10)
<223> OTHER INFORMATION: 2'-O-methylribonucleotide

<400> SEQUENCE: 54
cagagcucug                                                          10

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: phosphodiester

<400> SEQUENCE: 55
tgcatcgatg ca                                                       12

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: phosphodiester

<400> SEQUENCE: 56
acgtagctac gt                                                       12

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: phosphorothioate

<400> SEQUENCE: 57
tgcatcgatg ca                                                       12
```

```
<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: phosphorothioate

<400> SEQUENCE: 58
acgtagctac gt                                                              12

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphodiester

<400> SEQUENCE: 59
cagagctctg                                                                 10

<210> SEQ ID NO 60
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothiate
<220> FEATURE:
<221> NAME/KEY: modified_base
<222> LOCATION: (9)..(25)
<223> OTHER INFORMATION: 2'-OMe-ribonucleotide

<400> SEQUENCE: 60
tcgtcgttga gcucugaaag agcuc                                                25

<210> SEQ ID NO 61
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: phosphorothiate
<220> FEATURE:
<221> NAME/KEY: modified_base
<222> LOCATION: (9)..(29)
<223> OTHER INFORMATION: 2'-OMe-ribonucleotide

<400> SEQUENCE: 61
```
tcgtcgttga gcucucugaa agagagcuc                                    29

<210> SEQ ID NO 62
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothiate
<220> FEATURE:
<221> NAME/KEY: modified_base
<222> LOCATION: (9)..(33)
<223> OTHER INFORMATION: 2'-OMe-ribonucleotide

<400> SEQUENCE: 62
tcgtcgttga gcucucugug aaacagagag cuc                               33

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothiate
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine

<400> SEQUENCE: 63
tcntcnttgt gagctctgtg aaacagagct cac                               33

<210> SEQ ID NO 64
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothiate
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine

<400> SEQUENCE: 64 tcntcntt                                                            8

<210> SEQ ID NO 65

```
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothiate
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (20)..(33)
<223> OTHER INFORMATION: 2'-OMe-ribonucleotide

<400> SEQUENCE: 65
tcntcnttgt gagctctgtg aaacagagcu cac                                    33

<210> SEQ ID NO 66
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothiate
<220> FEATURE:
<221> NAME/KEY: modified_base
<222> LOCATION: (3)
<223> OTHER INFORMATION: 2'-deoxy-7-deazaguanoise
<220> FEATURE:
<221> NAME/KEY: modified_base
<222> LOCATION: (6)
<223> OTHER INFORMATION: 2'-deoxy-7-deazaguanoise

<400> SEQUENCE: 66 tcntcntt                                                                 8

<210> SEQ ID NO 67
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: phosphorothiate

<400> SEQUENCE: 67 agagag                                                                   6

<210> SEQ ID NO 68
<211> LENGTH: 6
<212> TYPE: DNA
<213> ORGANISM: Artificial Sequence
<220> FEATURE:
<223> OTHER INFORMATION: Description of Artificial Sequence: Synthetic
```

```
         oligonucleotide
<220> FEATURE:
<221> NAME/KEY: misc_feature
<222> LOCATION: (1)..(6)
<223> OTHER INFORMATION: phosphodiester

<400> SEQUENCE: 68 agagag                                                                    6

<210> SEQ ID NO 69
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothiate
<220> FEATURE:
<221> NAME/KEY: modified_base
<222> LOCATION: (20)..(33)
<223> OTHER INFORMATION: 2'-O-methylribonucleotide

<400> SEQUENCE: 69
tcgtcgttgt gagctctgtg aaacagagcu cac                                     33

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: phosphorothiate
<220> FEATURE:
<221> NAME/KEY: misc_feature
<222> LOCATION: (3)..(15)
<223> OTHER INFORMATION: phosphodiester
<220> FEATURE:
<221> NAME/KEY: misc_feature
<222> LOCATION: (16)..(20)
<223> OTHER INFORMATION: phosphorothiate

<400> SEQUENCE: 70
ggtgcatcga tgcaggggggg                                                   20

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothiate

<400> SEQUENCE: 71
gtgagctctg tgaaacagag ctcac                                              25

<210> SEQ ID NO 72
<211> LENGTH: 10
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothiate
<220> FEATURE:
<221> NAME/KEY: modified_base
<222> LOCATION: (1)..(10)
<223> OTHER INFORMATION: 2'-OMe-ribonucleotide

<400> SEQUENCE: 72
cagagcucug                                                              10

<210> SEQ ID NO 73
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothiate
<220> FEATURE:
<221> NAME/KEY: modified_base
<222> LOCATION: (1)..(25)
<223> OTHER INFORMATION: 2'-OMe-nucleoside

<400> SEQUENCE: 73
gugagcucug ugaaacagag cucac                                             25

<210> SEQ ID NO 74
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphodiester
<220> FEATURE:
<221> NAME/KEY: modified_base
<222> LOCATION: (1)..(10)
<223> OTHER INFORMATION: 2'-OMe-nucleoside

<400> SEQUENCE: 74
cagagcucug                                                              10

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothiate

<400> SEQUENCE: 75
ctcacctctg                                                              10

<210> SEQ ID NO 76
```

```
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothiate
<220> FEATURE:
<221> NAME/KEY: modified_base
<222> LOCATION: (1)..(10)
<223> OTHER INFORMATION: 2'-OMe-nucleoside

<400> SEQUENCE: 76
cucaccucug                                                         10
```

STABILIZED IMMUNOMODULATORY OLIGONUCLEOTIDES

RELATED APPLICATIONS

This application is a Continuation application which claims priority from U.S. application Ser. No. 10/865,245 filed Jun. 10, 2004, which claims the benefit of U.S. Provisional Application No. 60/477,608, filed Jun. 11, 2003, U.S. Provisional Application No. 60/499,038 filed Aug. 29, 2003, and U.S. Provisional Application No. 60/504,279 filed Sep. 18, 2003, which are incorporated by reference in their entirety.

BACKGROUND OF THE INVENTION

1. Field of the Invention

The present invention relates to the fields of molecular biology, immunology and medicine. More specifically, the invention relates to immunostimulatory oligonucleotides and therapeutic uses thereof.

2. Summary of the Related Art

The immune system has evolved to specifically recognize DNA that contains an unmethylated CpG dinucleotide motif, which commonly occurs in the DNA of pathogens such as bacteria and viruses. As a result, unmethylated CpG-containing DNA is potent stimulator of the vertebrate immune system. First reports of immune stimulation by DNA came from studies using bacterial DNA and short fragments of DNA containing palindromic sequences, both of which were double-stranded structures with phosphodiester backbones Tokunaga, T., et al., (*J. Natl. Cancer Inst.* 72: 955-962 (1984)) demonstrated potent anti-tumor activity for DNA isolated from *Mycobacterium bovis* BCG. Kataoka, T, et al., (*Jpn. J. Cancer Res.* 83: 244-247 (1992)), Hartmann et al. (*European Journal of Immunology* 33:1673-1641 (2003)), Marshall et al. Journal of Leukocyte Biology 73:781-792 (2003) showed a similar type of anti-tumor activity for synthetic oligodeoxynucleotides, the design of which was based on *Mycobacterium bovis* BCG cDNA sequences.

Sato, Y, et al., (*Science* 273: 352-354 (1996)) showed the importance of CpG-containing DNA in the application of DNA vaccines (see also Gurunathan S., et al. (*Annu. Rev. Immunol.* 18: 927-974 (2000)). Pisetsky, D. S., et al., (*Mol. Biol. Rep.* 18: 217-221 (1993)) and Krieg, A. M., et al., (*Nature* 374: 546-549 (1995)) showed that DNA containing unmethylated CpG-dinucleotides in specific sequence contexts (CpG DNA) activated the vertebrate immune system, leading to proliferation of B cells and activation of macrophages, monocytes, NK cells, and dendritic cells. In response to CpG DNA activation, immune cells secrete a number of cytokines including IL-12, IFN-γ, INF-α, IL-6 and TNF-α and express several co-stimulatory molecules (for example, see Pisetsky, D. S., et al. and Krieg, A. M., et al., supra).

Kandimalla, E. R., et al., (*Curr. Opin. Mol. Ther.* 4 122-129 (2002)) indicate that the presence and position of a CpG-dinucleotide and the sequences that flank it are critical for immunostimulatory activity. Agrawal, S., et al. (*Current Cancer Drug Targets* 1: 197-209 (2001)) discloses significant effects due to ribose modifications in the flanking sequences of the CpG oligonucleotides. These effects depend on the position and nature of substituents, including 2'-O-methoxyethoxy and 2'- or 3'-O-methyl groups. Yu, D., et al. (*Bioorg. Med. Chem.* 9: 2803-2808 (2001)) demonstrate that phosphate modifications can also increase or decrease immunostimulatory activity depending on their position. Yu D., et al. (*Bioorg. Med. Chem. Lett.* 11: 2263-2267 (2001)) and Yu D., et al. (*Bioorg. Med. Chem.* 11: 459-464 (2003)) disclose that activity can be increased by deletion of certain nucleobases. In addition Yu D., et al. (*Bioorg. Med. Chem.* 11: 459-464 (2003)) disclose that immunostimulatory activity can be increased by substitution of certain flanking nucleotides with non-nucleotidic linkers.

Yu D., et al. (*Bioorg. Med. Chem. Lett.* 10: 2585-2588 (2000)), Yu D., et al. (*Nucleic Acids Res.* 30: 4460-4469 (2002)), Yu D., et al. (*Biochem. Biophys. Res. Commun.* 297: 83-90 (2002)), Bhagat L., et al. (*Biochem. Biophys. Res. Commun.* 300: 853-861 (2003)) and Kandimalla E. R., et al. (*Nucleic Acids Res.* 31: 2393-2400 (2003) previously have shown that the 5'-terminus is involved in receptor recognition and that accessibility of this end is critical for activity. Kandimalla E. R., et al. (*Bioconj. Chem.* 13: 966-974 (2002)) disclose loss of immunostimulatory activity following 5'-terminal conjugation of ligands larger than fluorescein or a 5'-5' linked dinucleotide. As 3'-conjugation is without effect, changes in uptake cannot account for the results (Id.). However, there have not been any systematic studies to elucidate the role of secondary structure of DNA on the resulting immune response. The invention herein provides information on immunostimulation by immunostimulatory DNA with 5'- and 3'-hairpin loops or sticky ends that can form duplexes.

The ability of immunostimulatory DNA to induce Th1 cytokine production and promote CTL responses with enhanced immunoglobulin production has been used for treating a broad spectrum of disease indications including cancers, viral and bacterial infections, inflammatory disorders and as an adjuvant in immunotherapy. Thus, the benefits of improving or modulating immunostimulatory DNA activity are clear, and there remains a need in the art to develop improved immunostimulatory nucleic acids.

BRIEF SUMMARY OF THE INVENTION

The invention provides novel compositions of matter comprising immunostimulatory oligonucleotides with increased or decreased immunostimulatory properties. The invention also provides methods that enable the design of immunostimulatory oligonucleotides with increased or decreased immunostimulatory properties or with increased metabolic stability. The inventors have surprisingly discovered that the introduction of a secondary structure into the 3'-end or 5'-end of immunostimulatory oligonucleotides significantly impacts the immunostimulatory activity and stability of these oligonucleotides.

In a first aspect the invention provides an immunostimulatory nucleic acid. The immunostimulatory nucleic acid comprises an oligonucleotide sequence containing at least one dinucleotide selected from the group consisting of CpG, C*pG, C*pG* and CpG*, wherein C is cytidine or 2'-deoxycytidine, G is guanosine or 2' deoxyguanosine, C* is cytidine, 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain preferred embodiments the oligonucleotide sequence has a secondary structure at the 3'-end of the oligonucleotide sequence. In certain preferred embodiments, the immunostimulatory dinucleotide is not CpG.

In some embodiments, the immunostimulatory nucleic acid is from about 2 to about 50 nucleotides in length. In certain embodiments the immunostimulatory nucleic acid is from about 12 to about 26 nucleotides in length. In some embodiments, the oligonucleotides each have from about 3 to about 35 nucleoside residues, preferably from about 4 to about 30 nucleoside residues, more preferably from about 4 to about 20 nucleoside residues. In some embodiments, the oligonucleotides have from about 5 to about 18 or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

In certain embodiments, the immunostimulatory nucleic acid has a 3'-end stem loop secondary structure. In some embodiments, the immunostimulatory nucleic acid has a secondary structure at the 3'-end by way of hydrogen bonding with a complementary sequence. In certain embodiments, the immunostimulatory nucleic acid is selected from the group consisting of SEQ ID NOS: 2, 3, 4, 9, 12, 13, 14, 18, 19, 20, 21, 24, 25, 26, 27, 28, 29, 30, 32, 33, 34, 35, 36, 37 and 38.

In a second aspect, the invention provides a nucleic acid having reduced immunostimulatory activity. In this aspect the nucleic acid comprises an oligonucleotide sequence containing at least one dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs; G* is 2'-deoxy-7-deazaguanosine, 2'-deoxy-6-thioguanosine, arabinoguanosine, 2'-deoxy-2'-substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain preferred embodiments the oligonucleotide sequence has a secondary structure at the 3'-end of the oligonucleotide sequence. In certain preferred embodiments, the immunostimulatory dinucleotide is not CpG.

In some embodiments, the immunostimulatory nucleic acid is an oligonucleotide sequence from about 2 to about 50 nucleotides in length. In certain embodiments the immunostimulatory nucleic acid is an oligonucleotide sequence from about 12 to about 26 nucleotides in length.

In certain embodiments the nucleic acid having reduced immunostimulatory activity forms a 5'-end stem loop secondary structure. In some embodiments, the nucleic acid having reduced immunostimulatory activity has a secondary structure at the 5'-end by way of hydrogen bonding with a complementary sequence. In certain embodiments the nucleic acid having reduced immunostimulatory activity is selected from the group consisting of SEQ ID NOS: 5, 6, 7, 10, 15, 16 and 17.

In a third aspect the invention provides an immunostimulatory nucleic acid comprising at least two oligonucleotides, wherein the immunostimulatory nucleic acid has a secondary structure. In this aspect, the immunostimulatory nucleic acid comprises a structure as detailed in formula (I).

Domain A-Domain B-Domain C    (I)

Domains may be from about 2 to about 12 nucleotides in length. Domain A may be 5'-3' or 3'-5' or 2'-5' DNA, RNA, RNA-DNA, DNA-RNA having or not having a palindromic or self-complementary domain containing or not containing at least one dinucleotide selected from the group consisting of CpG, C*pG, C*pG* and CpG*, wherein C is cytidine or 2'-deoxycytidine, G is guanosine or 2' deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substitutedarabinocytidine, 2'O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G- is guanosine or 2' deoxyguanosine, 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs. In certain embodiments, Domain A will have more than one dinucleotide selected from the group consisting of CpG, C*pG, C*pG* and CpG*.

Domain B, as depicted by an "X" below, is a linker joining Domains A and C that may be a 3'-'S' linkage, a 2'-5' linkage, a 3'-3' linkage, a phosphate group, a nucleoside, or a non-nucleoside linker that may be aliphatic, aromatic, aryl, cyclic, chiral, achiral, a peptide, a carbohydrate, a lipid, a fatty acid, mono- tri- or hexapolyethylene glycol, or a heterocyclic moiety. In some embodiments, Domain B is preferably a non-nucleotidic linker connecting oligonucleotides of Domain A and Domain C, which are referred to as "immunomers".

Domain C may be 5'-3' or 3'-5', 2'-5' DNA, RNA, RNA-DNA, DNA-RNA Poly I-Poly C having or not having a palindromic or self-complementary sequence, which can or cannot have a dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain preferred embodiments, the immunostimulatory dinucleotide is not CpG. In certain preferred embodiments, Domain C does not have the dinucleotide CpG, C*pG, C*pG*, or CpG*.

In some embodiments, the oligonucleotides contained in formula (I) are from about 2 to about 50 nucleotides in length. In certain embodiments the oligonucleotides contained in formula (I) are from about 12 to about 26 nucleotides in length.

By way of non-limiting example, in certain embodiments of this aspect the immunostimulatory nucleic acid will have a structure as detailed in formula (II).

(II)

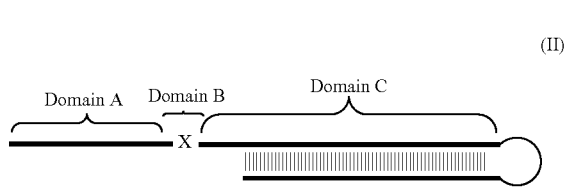

As one skilled in the art would recognize, there is a secondary structure element in the 3' end of the molecule in the form of an intramolecular stem-loop.

By way of non-limiting example, in certain embodiments of this aspect the immunostimulatory nucleic acid will have a structure as detailed in formula (III).

(III)

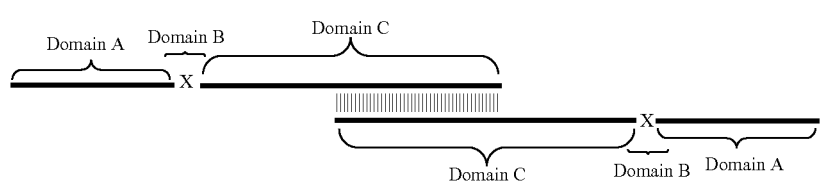

The structure depicted in formula (III) is referred to herein as a "terminal dimmer," since the 3' ends of the two molecules are blocked because the sequences of the two 3' ends are complementary allowing for intermolecular hydrogen bonding. In addition, domains A and A' may or may not be identical, domains B and B' may or may not be identical and domains C and C' may or may not be identical.

By way of non-limiting example, in certain embodiments of this aspect the immunostimulatory nucleic acid will have a structure as detailed in formula (IV).

(IV)

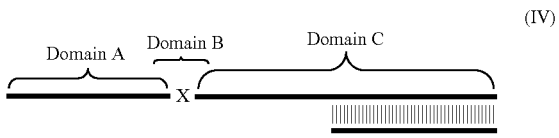

As would be recognized by one skilled in the art, the 3' end of the depicted molecule has a secondary structure because the complementary sequence of its 3' end is hydrogen bonded to this region.

In certain embodiments, the immunostimulatory nucleic acids of the invention have sequence selected from the group consisting of SEQ ID NOS: 1-38. In some embodiments, the immunostimulatory nucleic acids of the invention have a sequence selected from the group consisting of SEQ ID NOS: 39-68.

In a fourth aspect, the invention provides a method for reducing or eliminating the immunostimulatory activity of an oligonucleotide. The method comprises introducing at the 5'-end of the oligonucleotide a nucleic acid sequence comprising a secondary structure. In some embodiments of this aspect, the secondary structure is a stem-loop structure. In certain embodiments of this aspect, the secondary structure is obtained by hydrogen bonding a complementary sequence to the 5'-end of the oligonucleotide sequence.

In a fifth aspect, the invention provides a method for increasing the stability of an immunostimulatory oligonucleotide. The method comprises introducing at the 3'-end of the immunostimulatory oligonucleotide a nucleic acid sequence comprising a secondary structure. In some embodiments of this aspect, the secondary structure is a stem-loop structure. In certain embodiments of this aspect, the secondary structure is obtained by hydrogen bonding a complementary sequence to the 3'-end of the oligonucleotide sequence.

In a sixth aspect, the invention provides a method for modulating the immunostimulatory activity of an immunostimulatory oligonucleotide. The method comprises introducing at the 3'-end or the 5'-end of the immunostimulatory oligonucleotide a nucleic acid sequence comprising a secondary structure. In some embodiments of this aspect, the secondary structure is a stem-loop structure. In certain embodiments of this aspect, the secondary structure is obtained by hydrogen bonding a complementary sequence to the 3'-end or 5'-end of the oligonucleotide sequence.

In a seventh aspect the invention provides pharmaceutical compositions. These compositions comprise any one of the compositions disclosed in the first, second, third, fourth, fifth and sixth aspects of the invention either alone or in combination and a pharmaceutically acceptable carrier.

DETAILED DESCRIPTION OF THE PREFERRED EMBODIMENTS

Figure 1:
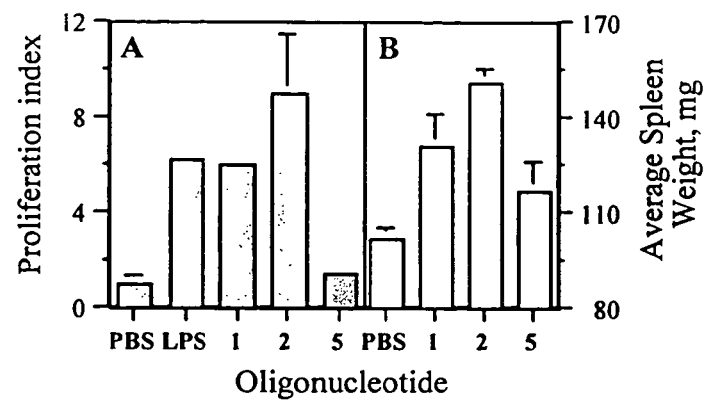
FIG. 1A is a schematic representation showing cell proliferation induced by oligos 1, 2, and 5 in BALB/c mouse spleen cell cultures at a concentration of 1.0 µg/mL
FIG. 1B is a schematic representation showing splenomegaly induced by oligos 1, 2, and 5 at a dose of 5 mg/kg administered intraperitoneally to BALB/c mice.

The invention provides novel compositions of matter comprising immunostimulatory oligonucleotides with increased or decreased immunostimulatory properties. The invention also provides methods that enable the design of immunostimulatory oligonucleotides with increased or decreased immunostimulatory properties or with increased metabolic stability. The inventors have surprisingly discovered that the introduction of a secondary structure into the 3'-end or 5'-end of immunostimulatory oligonucleotides significantly impacts the immunostimulatory activity and stability of these oligonucleotides.

The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

In a first aspect the invention provides an immunostimulatory nucleic acid. The immunostimulatory nucleic acid comprises an oligonucleotide sequence containing at least one dinucleotide selected from the group consisting of CpG, C*pG, C*pG* and CpG*, wherein C is cytidine or 2'-deoxycytidine, G is guanosine or 2' deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate and wherein the oligonucleotide sequence has a secondary structure at the 3'-end of the oligonucleotide sequence. In certain preferred embodiments, the immunostimulatory dinucleotide is not CpG.

In some embodiments, the immunostimulatory nucleic acid is from about 2 to about 50 nucleotides in length. In certain embodiments the immunostimulatory nucleic acid is from about 12 to about 26 nucleotides in length. In some embodiments, the oligonucleotides each have from about 3 to about 35 nucleoside residues, preferably from about 4 to about 30 nucleoside residues, more preferably from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

In certain embodiments, the immunostimulatory nucleic acid has a 3'-end stem loop secondary structure. In some embodiments, the immunostimulatory nucleic acid has a secondary structure at the 3'-end by way of hydrogen bonding with a complementary sequence. In certain embodiments, the immunostimulatory nucleic acid is selected from the group consisting of SEQ ID NOS: 2, 3, 4, 9, 12, 13, 14, 18, 19, 20, 21, 24, 25, 26, 27, 28, 29, 30, 32, 33, 34, 35, 36, 37 and 38.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, 2'-deoxypentfuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (RP)- or (SP)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

For purposes of the invention, the term "2'-substituted ribonucleoside" or "2'-substituted arabinoside" includes ribonucleosides or arabinonucleosides in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethoxyribonucleosides or 2'-O-methoxyethoxyarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2' substituted ribonucleotide region, and a deoxyribonucleotide region (see, e.g., Metelev and Agrawal, U.S. Pat. Nos. 5,652,355, 6,346,614 and 6,143,881).

As used herein, the term "secondary structure" refers to intramolecular and intermolecular hydrogen bonding. Intramolecular hydrogen bonding results in the formation of a stem-loop structure. Intermolecular hydrogen bonding results in the formation of a duplexed nucleic acid molecule.

As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above, for purposes of this invention.

As used herein, the term "complementary" means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

In a second aspect, the invention provides a nucleic acid having reduced immunostimulatory activity. In this aspect the nucleic acid comprises an oligonucleotide sequence containing at least one dinucleotide selected from the group consisting of CpG, C*pG, C*pG* and, CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-di deoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate and wherein the oligonucleotide sequence has a secondary structure at the 5'-end of the oligonucleotide sequence. In certain preferred embodiments, the immunostimulatory dinucleotide is not CpG.

In some embodiments, the immunostimulatory nucleic acid is an oligonucleotide sequence from about 2 to about 50 nucleotides in length. In certain embodiments the immunostimulatory nucleic acid is an oligonucleotide sequence from about 12 to about 26 nucleotides in length. In some embodiments, the oligonucleotides each have from about 3 to about 35 nucleoside residues, preferably from about 4 to about 30 nucleoside residues, more preferably from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

In certain embodiments the nucleic acid having reduced immunostimulatory activity forms a 5'-end stem loop secondary structure. In some embodiments, the nucleic acid having reduced immunostimulatory activity has a secondary structure at the 5'-end by way of hydrogen bonding with a complementary sequence. In certain embodiments the nucleic acid having reduced immunostimulatory activity is selected from the group consisting of SEQ ID NOS: 5, 6, 7, 10, 15, 16 and 17.

In a third aspect the invention provides an immunostimulatory nucleic acid comprising at least two oligonucleotides, wherein the immunostimulatory nucleic acid has a secondary structure. In this aspect, immunostimulatory nucleic acid comprises a structure as detailed in formula (I).

Domain A-Domain B-Domain C　　　　　(I)

Domains may be from about 2 to about 12 nucleotides in length. Domain A may be 5'-3' or 3'-5' or 2'-5' DNA, RNA, RNA-DNA, DNA-RNA having or not having a palindromic or self-complementary domain containing or not containing at least one dinucleotide selected from the group consisting of CpG, C*pG, C*pG* and cpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2' dideoxy-5-nitrocytosine, arabinocytidine, 2'-deoxy-2'-substitutedarabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain preferred embodiments, the immunostimulatory dinucleotide is not CpG.

In certain embodiments, Domain A will have more than one dinucleotide selected from the group consisting of CpG, C*pG, C*pG* and CpG*.

Domain B, as depicted by an "X" below, is a linker joining Domains A and C that may be a 3'-'5' linkage, a 2'-5' linkage, a 3'-3' linkage, a phosphate group, a nucleoside, or a non-nucleoside linker that may be aliphatic, aromatic, aryl, cyclic, chiral, achiral, a peptide, a carbohydrate, a lipid, a fatty acid, mono- tri- or hexapolyethylene glycol, or a heterocyclic moiety.

Domain C may be 5'-3' or 3'-5', 2'-5' DNA, RNA, RNA-DNA, DNA-RNA Poly I-Poly C having or not having a palindromic or self-complementary sequence, which can or cannot have a dinucleotide selected from the group consisting of CpG, C*pG, C*pG*, CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2' dideoxy-5-halocytosine, 2' dideoxy-5-halocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, other pyrimidine nucleoside analogs, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain preferred embodiments, the immunostimulatory dinucleotide is not CpG. In some embodiments, Domain B is preferably a non-nucleotidic linker connecting oligonucleotides of Domain A and Domain C, which are referred to as "immunomers." In certain preferred embodiments, Domain C does not have the dinucleotide CpG, C*pG, C*pG* or CpG*.

In some embodiments, the oligonucleotides of contained in formula (I) are from about 2 to about 50 nucleotides in length. In certain embodiments the oligonucleotides of contained in formula (I) are from about 12 to about 26 nucleotides in length. In some embodiments, the oligonucleotides each have from about 3 to about 35 nucleoside residues, preferably from about 4 to about 30 nucleoside residues, more preferably from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

By way of non-limiting example, in certain embodiments of this aspect the immunostimulatory nucleic acid will have a structure as detailed in formula (II).

(II)

Domain A　Domain B　　Domain C

As one skilled in the art would recognize, there is a secondary structure element in the 3' end of the molecule in the form of an intramolecular stem-loop.

By way of non-limiting example, in certain embodiments of this aspect the immunostimulatory nucleic acid will have a structure as detailed in formula (III)

(III)

Domain A　Domain B　Domain C

Domain C　Domain B　Domain A

The structure depicted in formula (III) is referred to herein as a "terminal dimmer," since the 3' ends of the two molecules are blocked because the sequences of the two 3' ends are complementary allowing for intermolecular hydrogen bonding. In addition, domains A and A' may or may not be identical, domains B and B' may or may not be identical and domains C and C' may or may not be identical.

By way of non-limiting example, in certain embodiments of this aspect the immunostimulatory nucleic acid will have a structure as detailed in formula (IV).

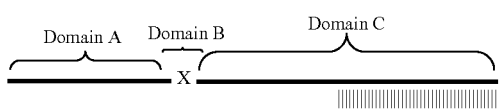

(IV)

As would be recognized by one skilled in the art, the 3' end of the depicted molecule has a secondary structure because the complementary sequence of its 3' end is hydrogen bonded to this region. In certain embodiments, a molecule such as a ligand may be attached to the 3'-end in order to facilitate cellular uptake or improve stability of the molecule.

Non-limiting examples of some nucleic acid molecules of the invention are presented in Table 1.

TABLE 1

| SEQ ID NO: | Sequence* | Structure |
|---|---|---|
| 1 | 5'-CTGTCTGACGTTCTCTG-3' | 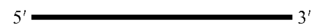 |
| 2 | 5'-CTGTCTGACGTTCTCTG-GAA-CAGAG-3' | 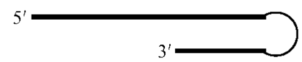 |
| 3 | 5'-CTGTCTGACGTTCTCTG-GAA-CAGAGAACGTC-3' | 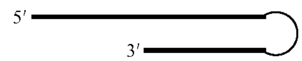 |
| 4 | 5'-CTGTCTGACGTTCTCTG-GAA-CAGAGAACGTCAGACAG-3' | 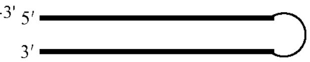 |
| 5 | 5'-GACAG-GAA-CTGTCTGACGTTCTCTG-3' | 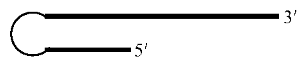 |
| 6 | 5'-AACGTCAGACAG-GAA-CTGTCTGACGTTCTCTG-3' | 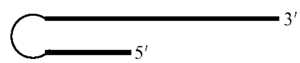 |
| 7 | 5'-CAGAGAACGTCAGACAG-GAA-CTGTCTGACGTTCTCTG-3' | 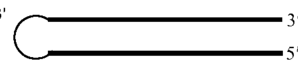 |
| 8 | 5'-CTATCTGACGTTCTCTGT-3' | 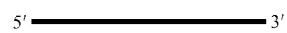 |
| 9 | 5'-CTATCTGACGTTCTCTGT-gtgatcac-3' | 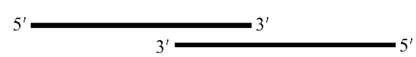 |
| 10 | 5'-gtgatcac-CTATCTGACGTTCTCTGT-3' | 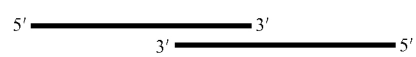 |
| 11 | 5'-CTGTCTGTCGTTCTCTG-3' | 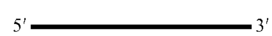 |
| 12 | 5'-CTGTCTGTCGTTCTCTG-GAA-CAGAG-3' | 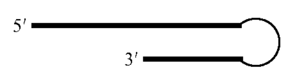 |
| 13 | 5'-CTGTCTGTCGTTCTCTG-GAA-CAGAGAACGAC-3' | 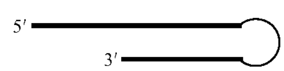 |
| 14 | 5'-CTGTCTGTCGTTCTCTG-GAA-CAGAGAACGACAGACAG-3' | 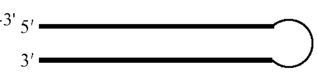 |
| 15 | 5'-GACAG-GAA-CTGTCTGTCGTTCTCTG-3' | 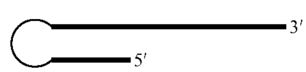 |
| 16 | 5'-AACGACAGACAG-GAA-CTGTCTGACGTTCTCTG-3' | 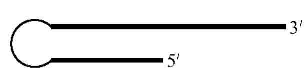 |
| 17 | 5'-CAGAGAACGACAGACAG-GAA-CTGTCTGTCGTTCTCTG-3' | 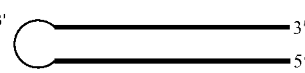 |

TABLE 1-continued

| SEQ ID NO: | Sequence* | Structure |
|---|---|---|
| 18 | 5'-TCGTCGTT-GAGCTCT-GAA-AGAGCTC-3' | 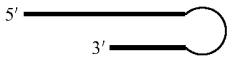 |
| 19 | 5'-TCGTCGTT-GTGAGCTCTGT-GAA-ACAGAGCTCAC-3' | 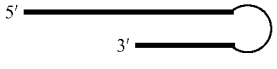 |
| 20 | 5'-TCGTCGTT-GCACAGAGCTCTGCT-GAA-AGCAGAGCTCTGTGC-3' | 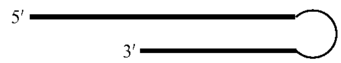 |
| 21 | 5'-TCGTCGTT-GCTGACAGAGCTCTGCTAT-GAA-ATAGCAGAGCTCTGTCAGC-3' | 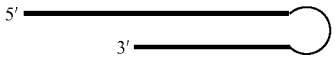 |
| 22 | 5'-TCGTCGTT-GTGCTCT-GAA-CTTGCTC-3' | 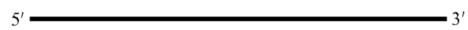 |
| 23 | 5'-TCGTCGTT-GTGTGCTCTGT-GAA-CATCAGTCTAC-3' | 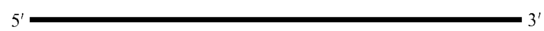 |
| 24 | 5'-TCGTCGTT-gagctct-GAA-agagctc-3' | 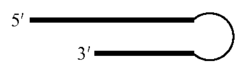 |
| 25 | 5'-TCGTCGTT-gtgagctctgt-GAA-acagagctcac-3' | 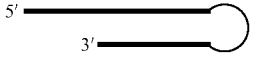 |
| 26 | 5'-TCGTCGTT-GAGCTCT-GAA-AGAGCTC-3' | 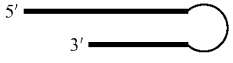 |
| 27 | 5'-TCGTCGTT-GTGAGCTCTGT-GAA-ACAGAGCTCAC-3' | 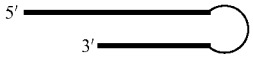 |
| 28 | 5'-TCGTCGTT-GAGCTCT-GAA-AGAGCTC-3' | 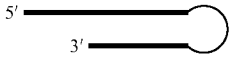 |
| 29 | 5'-TCGTCGTT-GAGCTCT-GAA-AGAGCTC-3' | 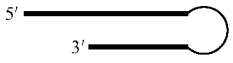 |
| 30 | 5'-TGCTGCTT-GAGCTCT-GAA-AGAGCTC-3' | 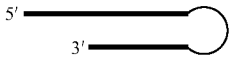 |
| 31 | 5'-TCTTGACGTTCTCTCT-3' | 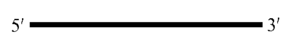 |
| 32 | 5'-TCTTGACGTTCTCTCT-GAA-AGAGAG-3' | 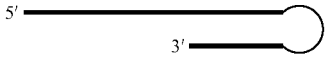 |
| 33 | 5'-TCTTGACGTTCTCTCT-GAA-agagag-3' | 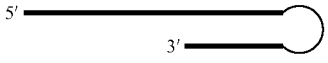 |
| 34 | 5'-tcttgacgttctctct-GAA-AGAGAG-3' | 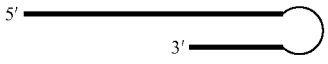 |
| 35 | 5'-tcttgacgttctctct-GAA-agagag-3' | 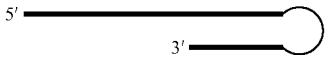 |
| 36 | 5'-tcttgacgttctctct-gaa-agagag-3' | 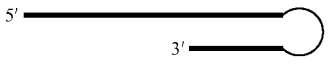 |
| 37 and 67 | 5'-TCTTGACGTTCTCTCT-X-AGAGAG-3' | 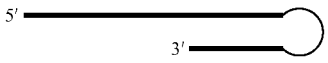 |

TABLE 1-continued

| SEQ ID NO: | Sequence* | Structure |
|---|---|---|
| 38 and 68 | 5'-tcttgacgttctctct-X-agagag-3' | 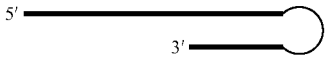 |

*upper case-PS; lower case-PO; Bold-2'-O-methyl-ribonucleotides (in 26 and 27); G-2'-deoxy-7-deaza-G (in 28); <u>G</u>-araG (in 29); X-C3-linker (in 37 and 38).

Alternatively, the nucleic acid molecule of the invention can be two immunomers linked by way of a non-nucleotidic linker. Non-limiting representative examples of these molecules are presented in Table 2.

TABLE 2

| Immunomer No. | SEQ ID NO: | Sequence* | Structure |
|---|---|---|---|
| 39 | 39 and 47 | 5'-TCGTCGTT-X-GTCTCGAGAC-5' | 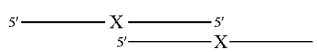 |
| 40 | 39 and 47 | 5'-TCGTCGTT-XX-GTCTCGAGAC-5' | 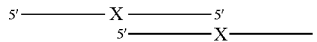 |
| 41 | 39 and 47 | 5'-TCGTCGTT-XXX-GTCTCGAGAC-5' | 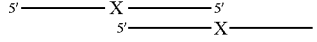 |
| 42 | 39 and 47 | 5'-TCGTCGTT-Y-GTCTCGAGAC-5' | 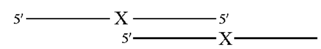 |
| 43 | 39 and 47 | 5'-TCGTCGTT-Z-GTCTCGAGAC-5' | 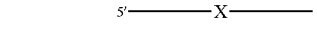 |
| 44 | 39 and 48 | 5'-TCGTCGTT-XXX-GUCUCGAGAC-5' | 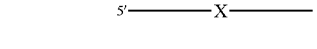 |
| 45 | 40 and 47 | 5'-TCGTCGTT-XXX-GTCTCGAGAC-5' | 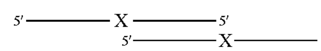 |
| 46 | 41 and 47 | 5'-TTGTGCTT-XXX-GTCTCGAGAC-5' | 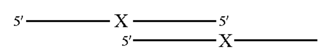 |
| 47 | 39 and 49 | 5'-TCGTCGTT-XXX-GTCTCCACAC-5' | 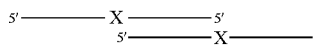 |
| 48 | 39 and 50 | 5'-TCGTCGTT-XXX-ccgtagctacGG-5' | 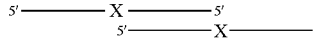 |
| 49 | 39 and 50 | 5'-TCGTCGTT-XX-ccgtagctacGG-5' | 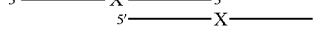 |
| 50 | 39 and 50 | 5'-TCGTCGTT- X-ccgtagctacGG-5' | 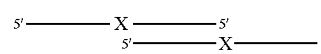 |
| 51 | 39 and 50 | 5'-TCGTCGTT-3'-3'-ccgtagctacGG-5' | 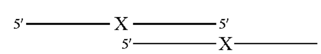 |
| 52 | 39 and 50 | 5'-TCGTCGTT-Y-ccgtagctacGG-5' | 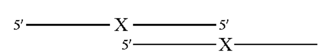 |
| 53 | 39 and 50 | 5'-TCGTCGTT-Z-ccgtagctacGG-5' | 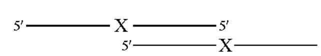 |
| 54 | 39 and 51 | 5'-TCGTCGTT-XXX-ctcgag-5' | 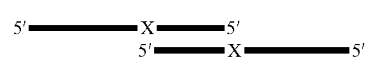 |
| 55 | 39 and 52 | 5'-TCGTCGTT-XXX-ctgtctcgagacag-5' | 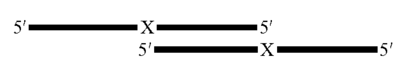 |
| 56 | 39 and 53 | 5'-TCGTCGTT-XXX-cgactgtctcgagacagtcg-5' |  or |

TABLE 2-continued

| Immunomer No. | SEQ ID NO: | Sequence* | Structure |
|---|---|---|---|
| 57 | 39 and 54 | 5'-TCGTCGTT-XXX-gucucgagac-5' | 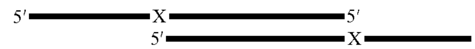 |
| 58 | 42, 55, and 42 | 5'-TCGTCGTTG-X-tgcatcgatgca-3'-X-3'-GTTGCTGCT-5' | 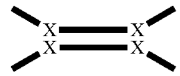 |
| 59 | 42, 56, and 42 | 5'-TCGTCGTTG-3'-X-3'-tgcatcgatgca-X-GTTGCTGCT-5' | 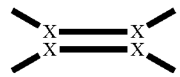 |
| 60 | 42, 57, and 42 | 5'-TCGTCGTTG-X-TGCATCGATGCA-3'-X-3'-GTTGCTGCT-5' | 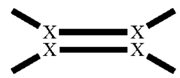 |
| 61 | 42, 58, and 42 | 5'-TCGTCGTTG-3'-X-3'-TGCATCGATGCA-X-GTTGCTGCT-5' | 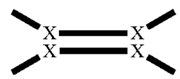 |
| 62 | 43, 57, and 43 | 5'-tcgtcgttg-X-TGCATCGATGCA-3'-X-3'-gttgctgct-5' | 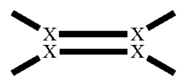 |
| 63 | 43, 58, and 43 | 5'-tcgtcgttg-3'-X-3'-TGCATCGATGCA-X-gttgctgct-5' | 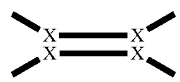 |
| 64 | 44 and 59 | 5'-tcgtcgtt-XXX-gtctcgagac-5' | 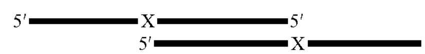 |
| 65 | 39 and 59 | 5'-TCGTCGTT-XXX-gtctcgagac-5' | 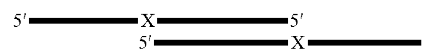 |
| 66 | 42 and 55 | 5'-TCGTCGTTG-X-tgcatcgatgca-3' | 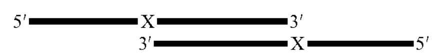 |
| 67 | 45 | 5'-TCGTCGTTGtgcatcgatgca-3' | 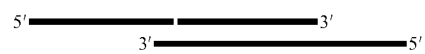 |
| 68 | 46 | 5'-tcgtcgttgTGCATCGATGCA-3' | 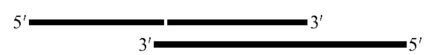 |

*Upper case-PS; lower case-PO, X-C3-linker; Y-tetraethyleneglycol linker; Z-hexaethyleneglycol linker, bold-2'-O-methylribonucleotides (in 44 and 57); G-2'-deoxy-7-deaza-G (in 45).

In certain embodiments, the immunostimulatory nucleic acids of the invention have sequence selected from the group consisting of SEQ ID NOS: 1-38. In some embodiments, the immunostimulatory nucleic acids of the invention have a sequence selected from the group consisting of SEQ ID NOS: 39-68.

In certain embodiments of the invention, at least one immunostimulatory oligonucleotide of the invention comprises an immunostimulatory dinucleotide of the formula 5'-Pyr-Pur-3', wherein Pyr is a natural pyrimidine nucleoside or analog thereof and Pur is a natural purine nucleoside or analog thereof. As used herein, the term "pyrimidine nucleoside" refers to a nucleoside wherein the base component of the nucleoside is a pyrimidine base. Similarly, the term "purine nucleoside" refers to a nucleoside wherein the base component of the nucleoside is a purine base. For purposes of the invention, a "synthetic" pyrimidine or purine nucleoside includes a non-naturally occurring pyrimidine or purine base, a non-naturally occurring sugar moiety, or a combination thereof.

Preferred pyrimidine nucleosides in the immunostimulatory oligonucleotides and/or immunomers used in the method according to the invention have the structure (I):

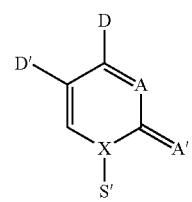

(V)

wherein:

D is a hydrogen bond donor;

D' is selected from the group consisting of hydrogen, hydrogen bond donor, hydrogen bond acceptor, hydrophilic group, hydrophobic group, electron withdrawing group and electron donating group;

A is a hydrogen bond acceptor or a hydrophilic group;

A' is selected from the group consisting of hydrogen bond acceptor, hydrophilic group, hydrophobic group, electron withdrawing group and electron donating group;

X is carbon or nitrogen; and

S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C=O, C=S, and the ring nitrogen atoms of an aromatic heterocycle, e.g., N3 of cytosine.

In some embodiments, the base moiety in (I) is a non-naturally occurring pyrimidine base. Examples of preferred non-naturally occurring pyrimidine bases include, without limitation, 5-hydroxycytosine, 5-hydroxymethylcytosine, N4-alkylcytosine, preferably N4-ethylcytosine, and 4-thiouracil. In some embodiments, the sugar moiety S' in (I) is a non-naturally occurring sugar moiety. For purposes of the present invention, a "naturally occurring sugar moiety" is a sugar moiety that occurs naturally as part of nucleic acid, e.g., ribose and 2'-deoxyribose, and a "non-naturally occurring sugar moiety" is any sugar that does not occur naturally as part of a nucleic acid, but which can be used in the backbone for an oligonucleotide, e.g, hexose. Arabinose and arabinose derivatives are examples of preferred sugar moieties.

Preferred purine nucleoside analogs in immunostimulatory oligonucleotides and/or immunomers used in the method according to the invention have the structure (II):

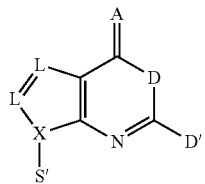

(VI)

wherein:

D is a hydrogen bond donor;

D' is selected from the group consisting of hydrogen, hydrogen bond donor, and hydrophilic group;

A is a hydrogen bond acceptor or a hydrophilic group;

X is carbon or nitrogen;

each L is independently selected from the group consisting of C, O, N and S; and S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$—, —SH and —OH. Preferred hydrogen bond acceptors include, without limitation, C=O, C=S, —NO$_2$ and the ring nitrogen atoms of an aromatic heterocycle, e.g., N1 of guanine.

In some embodiments, the base moiety in (VI) is a non-naturally occurring purine base. Examples of preferred non-naturally occurring purine bases include, without limitation, 6-thioguanine and 7-deazaguanine. In some embodiments, the sugar moiety S' in (II) is a naturally occurring sugar moiety, as described above for structure (I).

In a fourth aspect, the invention provides a method for reducing or eliminating the immunostimulatory activity of an oligonucleotide. The method comprises introducing at the 5'-end of a CpG-containing oligonucleotide a nucleic acid sequence comprising a secondary structure. In some embodiments of this aspect, the secondary structure is a stem-loop structure. In certain embodiments of this aspect, the secondary structure is obtained by hydrogen bonding a complementary sequence to the 5'-end of the oligonucleotide sequence.

In a fifth aspect, the invention provides a method for increasing the stability of an immunostimulatory oligonucleotide. The method comprises introducing at the 3'-end of the immunostimulatory oligonucleotide a nucleic acid sequence comprising a secondary structure. In some embodiments of this aspect, the secondary structure is a stem-loop structure. In certain embodiments of this aspect, the secondary structure is obtained by hydrogen bonding a complementary sequence to the 3'-end of the oligonucleotide sequence.

In a sixth aspect, the invention provides a method for modulating the immunostimulatory activity of an immunostimulatory oligonucleotide. The method comprises introducing at the 3'-end or the 5'-end of the immunostimulatory oligonucleotide a nucleic acid sequence comprising a secondary structure. In some embodiments of this aspect, the secondary structure is a stem-loop structure. In certain embodiments of this aspect, the secondary structure is obtained by hydrogen bonding a complementary sequence to the 3'-end or 5'-end of the oligonucleotide sequence.

As used herein, the term "modulating" or "modulate" means to increase or decrease the immunostimulatory activity of an immunostimulatory nucleic acid relative to that of the parent immunostimulatory nucleic acid.

In a seventh aspect the invention provides pharmaceutical compositions. These compositions comprise any one of the compositions disclosed in the first, second and third aspects of the invention either alone or in combination and a pharmaceutically acceptable carrier.

As used herein, this term "physiologically acceptable" refers to a material that does not interfere with the effectiveness of the compositions of the first, second or third aspects of the invention and is compatible with a biological system such as a cell, cell culture, tissue, or organism. Preferably, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., Remington's Pharmaceutical Sciences, 18th Edition, ed. A. Gennaro, Mack Publishing Co., Easton, Pa., 1990, ISBN: 0-912734-04-3.

Pharmaceutical compositions of the invention may also include a cancer vaccine, including a cancer vaccine selected from the group consisting of EFG, Anti-idiotypic cancer vaccines, Gp75 antigen, GMK melanoma vaccine, MGV ganglioside conjugate vaccine, Her2/new, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-vased vaccine, PACIS, BCG vaccine, TA-HPV, TA-CIN, DISC-virus and ImmunCyst/TheraCys.

In various embodiments of the invention, the compositions of the first, second, third, fourth, fifth or sixth aspects of the invention may be covalently linked to an antigen or otherwise operatively associated with an antigen. As used herein, the term "operatively associated with" refers to any association that maintains the activity of both the compositions of the first, second or third aspects of the invention and the antigen. Non-limiting examples of such operative associations include being part of the same liposome or other such delivery vehicle or reagent. In embodiments wherein the compositions of the first, second or third aspects of the invention are covalently linked to an antigen, such covalent linkage preferably is at any position on the compositions of the first, second or third aspects of the invention other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In various embodiments of the invention, the compositions of the first, second, third, fourth, fifth or sixth aspects of the invention may include an oligonucleotide with antisense activity. As used herein, "antisense activity" means that the oligonucleotide, when introduced into a cell or an animal, causes a reduction in the expression of the gene to which it is complementary.

In various embodiments of the invention, the compositions of the first, second, third, fourth, fifth or sixth aspects of the invention may include an oligonucleotide sequence that is an aptamer. Aptamers are nucleic acid molecules that have been selected from random pools based on their ability to bind other molecules. Aptamers have been selected which bind nucleic acids, proteins, small organic compounds, and even entire organisms. These novel molecules have many potential uses in medicine and technology (see, e.g., Burgstaller P., et al. *Curr Opin Drug Discov Devel.* 5: 690-700 (2002)).

The pharmaceutical compositions of the invention may be administered by any suitable route, including, without limitation, parenteral, oral, sublingual, transdermal, topical, intranasal, aerosol, intraocular, intratracheal, intrarectal, vaginal, by gene gun, dermal patch or in eye drop or mouthwash form. The pharmaceutical compositions can be delivered using known procedures at dosages and for periods of time effective obtain the desired effect, e.g. the treatment of cancer, the treatment of infection and the treatment of autoimmune diseases. When administered systemically, the pharmaceutical compositions are preferably administered at a sufficient dosage to attain a blood level of the compositions of the first, second and/or third aspects of the invention from about 0.0001 micromolar to about 10 micromolar. For localized administration, much lower concentrations than this may be effective, and much higher concentrations may be tolerated. Preferably, a total dosage of immunostimulatory oligonucleotide and/or immunomer ranges from about 0.0001 mg per patient per day to about 200 mg per kg body weight per day. It may be desirable to administer simultaneously, or sequentially a therapeutically effective amount of one or more of the therapeutic compositions of the invention to an individual as a single treatment episode.

Figure 9:
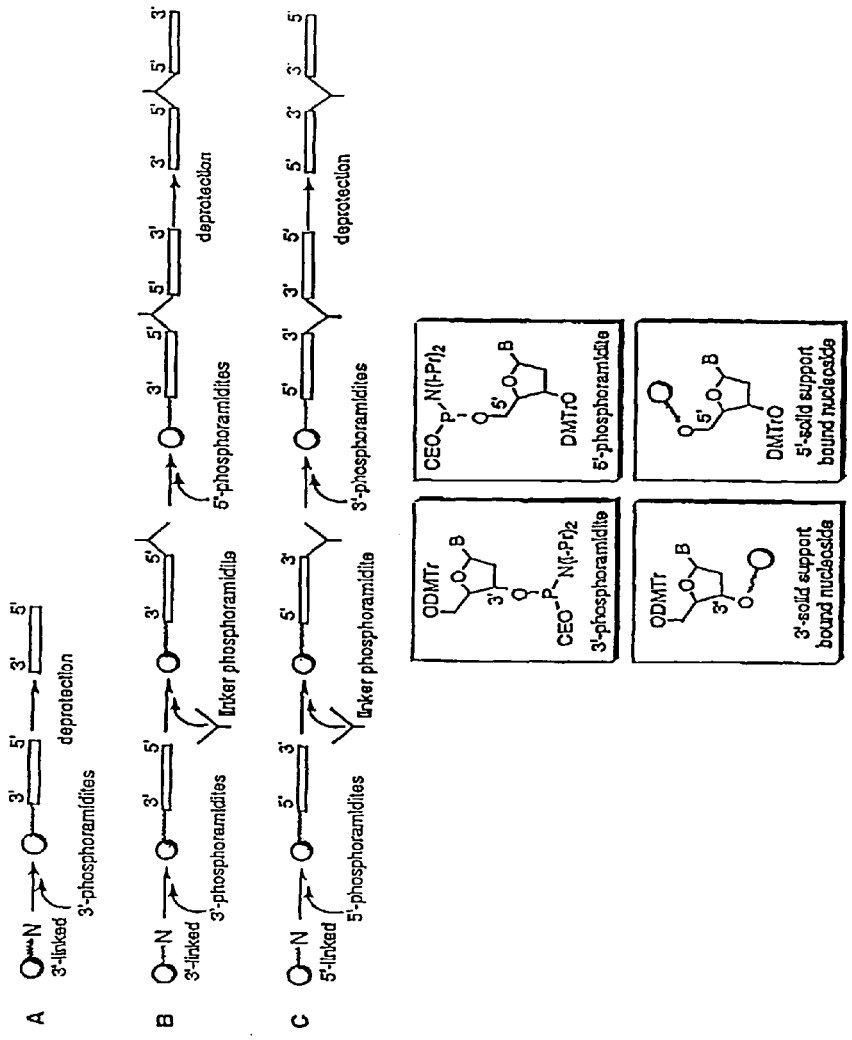
FIG. 9 is a synthetic scheme for the parallel synthesis of immunomers of the invention. DMTr=4,4'-dimethoxytrityl; CE=cyanoethyl.
Figure 10:
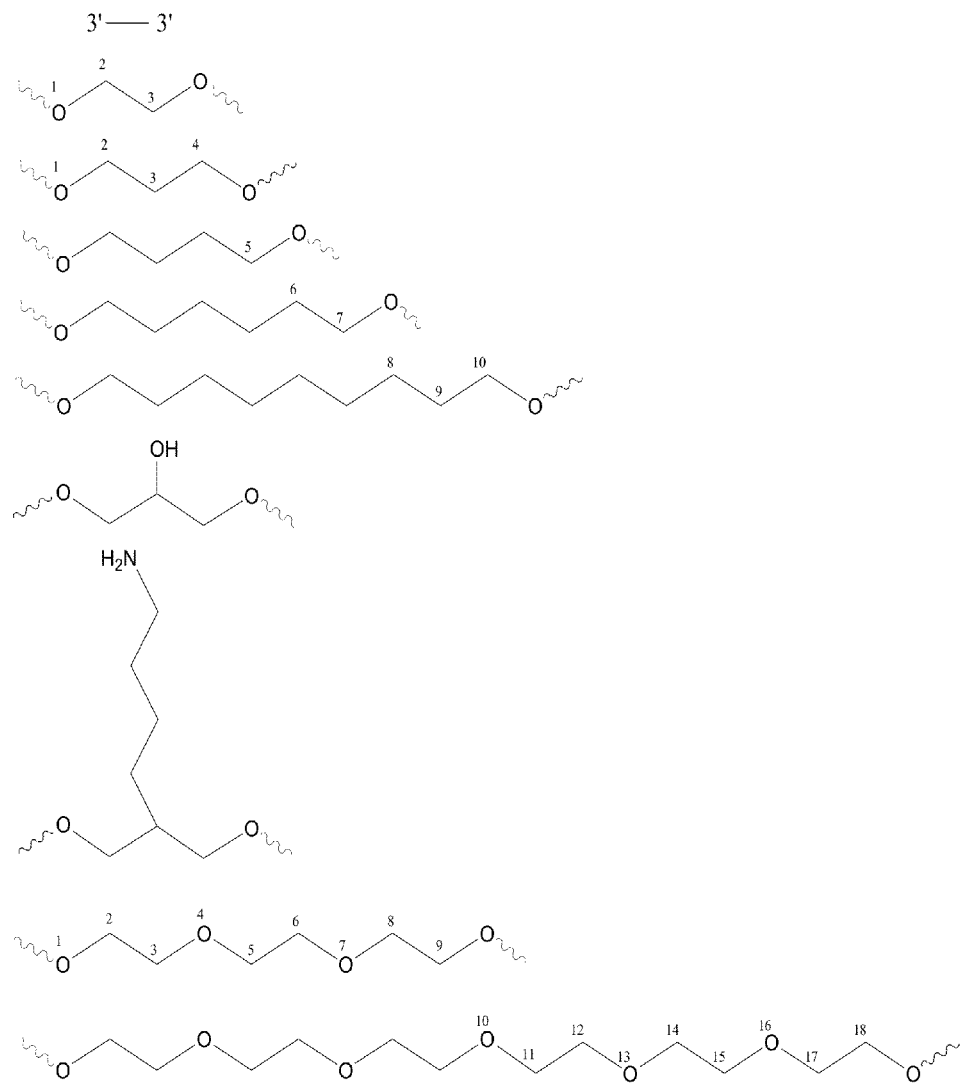
FIG. 10 depicts a group of representative small molecule linkers suitable for linear synthesis of immumomers of the invention.
Figure 11:
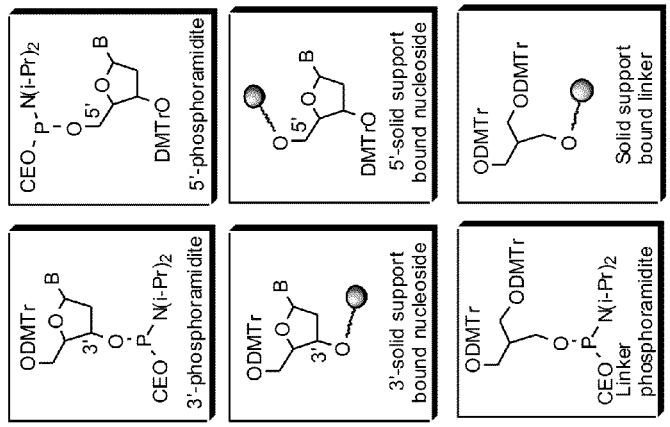
FIG. 11 is a synthetic scheme for the linear synthesis of immunomers of the invention. DMTr=4,4'-dimethoxytrityl; CE=cyanoethyl.
Figure 11:
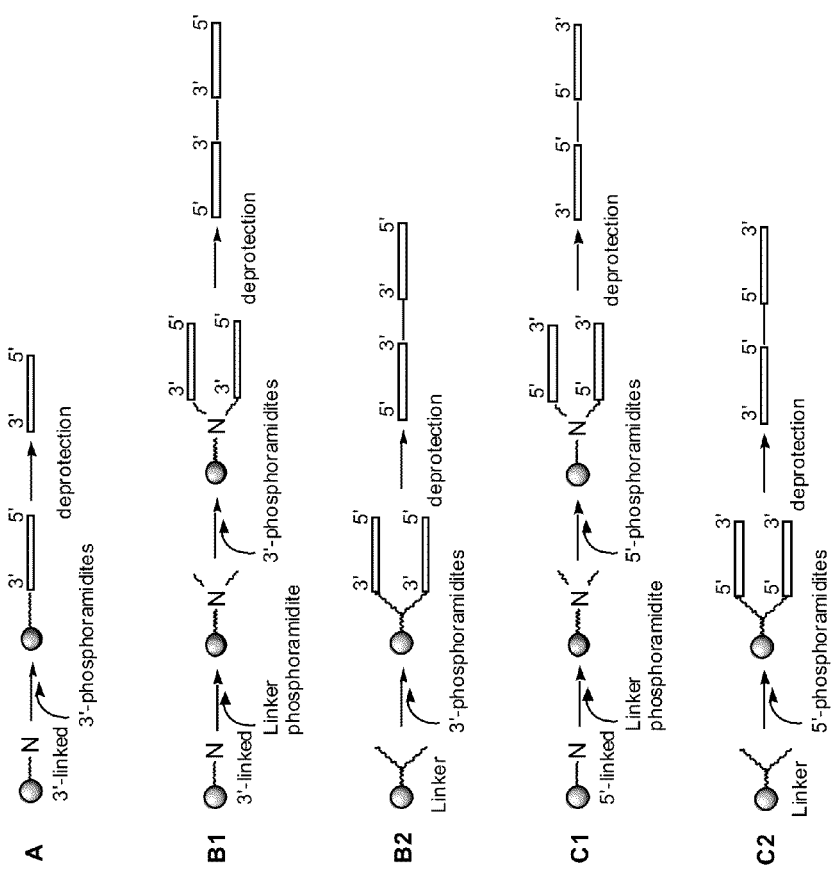

In addition, when immunostimulatory oligonucleotides were created as immunomers the following protocols were used for synthesis. The immunostimulatory oligonucleotides and/or immunomers of the invention may conveniently be synthesized using an automated synthesizer and phosphoramidite approach as schematically depicted in FIGS. 9 and 11. In some embodiments, the immunostimulatory oligonucleotides and/or immunomers are synthesized by a linear synthesis approach (see FIG. 9). Representative linkers for this synthesis are presented in FIG. 10. As used herein, the term "linear synthesis" refers to a synthesis that starts at one end of the immunomer and progresses linearly to the other end. Linear synthesis permits incorporation of either identical or un-identical (in terms of length, base composition and/or chemical modifications incorporated) monomeric units into the immunostimulatory oligonucleotides and/or immunomers.

Figure 12:
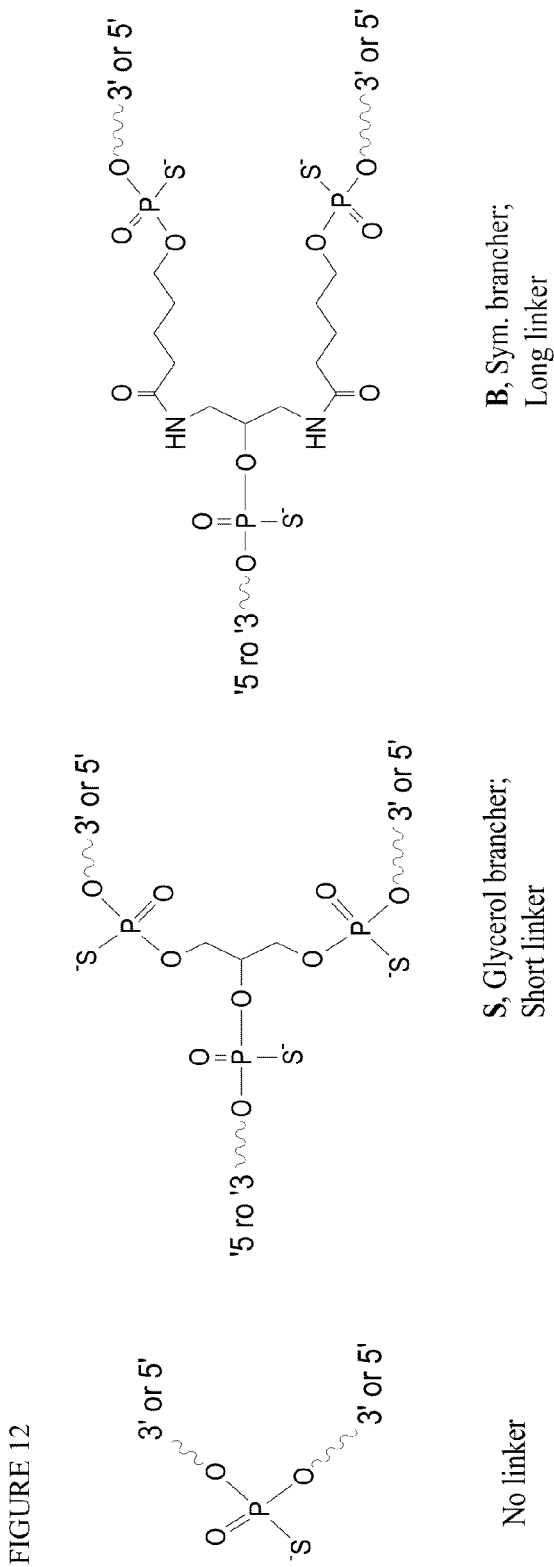
FIG. 12 depicts a group of representative small molecule linkers suitable for parallel synthesis of immunomers of the invention.

An alternative mode of synthesis for immunomers is "parallel synthesis", in which synthesis proceeds outward from a central linker moiety (see FIG. 11). Representative linkers for this method of synthesis are presented in FIG. 12. A solid support attached linker can be used for parallel synthesis, as is described in U.S. Pat. No. 5,912,332. Alternatively, a universal solid support, such as phosphate attached to controlled pore glass support, can be used.

Parallel synthesis of immunomers has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immunomer product.

At the end of the synthesis by either linear synthesis or parallel synthesis protocols, the immunostimulatory oligonucleotides or immunomers according to the invention may conveniently be deprotected with concentrated ammonia solution or as recommended by the phosphoramidite supplier, if a modified nucleoside is incorporated. The product immunostimulatory oligonucleotides and/or immunomer is preferably purified by reversed phase HPLC, detritylated, desalted and dialyzed.

The stimulatory domain of CpG DNAs 18-21 contained a human specific 'GTCGTT' motif at the 5'-end. In the structural domain region, complementary sequences that formed 7, 11, 15, or 19 base-pair (bp) hairpin stem-loop structures were incorporated adjacent to the 3'-end of the stimulatory domain (Table 3). Self-stabilized CpG DNAs were designed such that the stimulatory domain did not contain any structural motifs (base-pairing) and CpG stimulatory motifs were not present in the structural domain. Both a stimulatory motif and a secondary structure in CpG DNAs are required for pDC activation. CpG DNAs induced strong concentration-dependent proliferation of human B cells in culture. However, B-cell proliferation was not dependent on the length of the hairpin duplex. The ability of self-stabilized CpG DNAs to activate both pDCs and B cells may permit the development of therapeutic agents for use against cancer, asthma, allergy, and infectious diseases and as adjuvant more potent than those that stimulate either B cells or pDCs.

Sequence 22 had a stimulatory domain but did not contain the required complementarity to form a hairpin structure at its 3'-end (structural domain). On the contrary, CpG DNA 30 formed a hairpin structure (structural domain) but did not have a stimulatory motif (Table 3). Sequence 69, an analog of sequence 19, contained 2'-O-methyl-ribonucleotides in one of the strands of the hairpin sequence.

The formation of stable hairpin structures by CpG DNAs was confirmed by thermal melting (Table 3) and EMSA studies. As expected CpG DNAs 18-21 showed bands with required mobility on a non-denaturing polyacrlyamide gel compared with oligonucleotide markers of different lengths and structures confirmed hairpin structure formation (data not shown).

Figure 13:
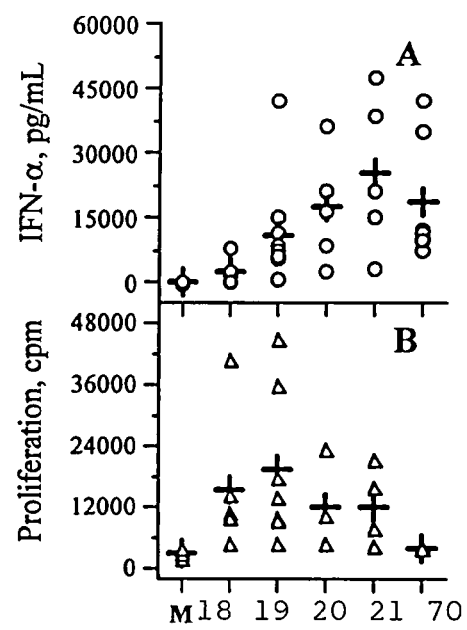
FIG. 13 Self-stabilized CpG DNAs induce (A) IFN-α secretion by human pDCs and (B) human B-cell proliferation in cultures. (A) pDCs were isolated from human PBMCs obtained from 5-8 healthy donors and stimulated with 10 μg/mL of CpG DNAs for 24 hr and the supernatants were assayed for IFN-α secretion by ELISA. (B) B cells were isolated from human PBMCs obtained from 4-7 healthy donors, stimulated with 1 μg/mL of CpG DNAs for 72 hr, and [$^3$H]-thymidine uptake was measured. Symbols represent data obtained with each donor and plus sign represents average value of all donors in both the panels.

Human pDCs express TLR9 and are believed to be the main source of CpG DNA-induced IFN-α. CpG DNAs 18-21 induced the production of IFN-α in human pDC cultures as shown in FIG. 13. The levels of IFN-α secretion depended on the length of the hairpin duplex structure. CpG DNA 21, which formed a 19-bp duplex, induced the highest levels of IFN-α (FIG. 13). While the response varied from donor to donor, the trend was consistent among the CpG DNAs (FIG. 13). CpG DNA 70, a palindromic CpG oligo containing poly (dG) sequences and known to stimulate human pDCs, was used as a positive control.

Figure 14:
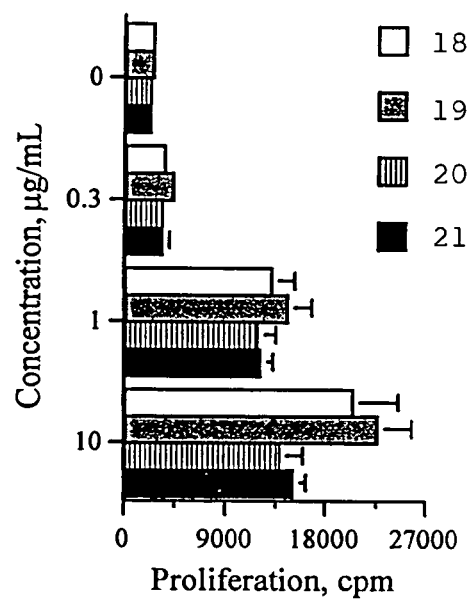
FIG. 14 CpG DNA concentration dependence of human B cell proliferation. B cells were isolated from human PBMCs obtained from 4-6 healthy donors, stimulated with different concentrations of CpG DNAs for 72 hr. Data shown are average±SD.

All four CpG DNAs induced strong concentration-dependent proliferation of human B cells in culture (FIG. 14). However, B-cell proliferation was not dependent on the length of the hairpin duplex (FIG. 13).

Figure 15:
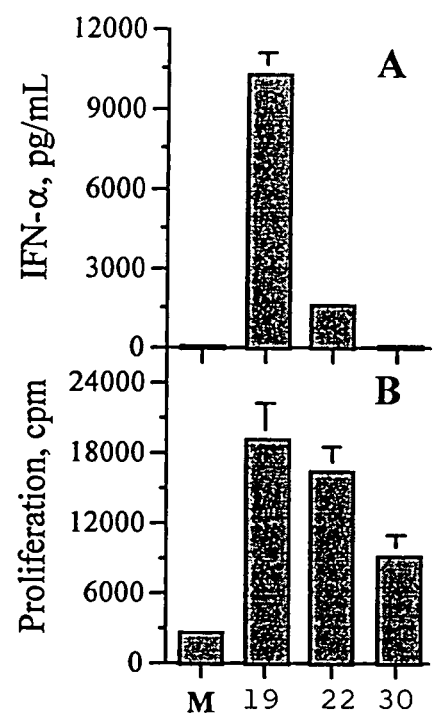
FIG. 15 (A) The presence of a CpG motif and secondary structure are required for induction of IFN-α secretion by human pDCs. Data shown are average±SD of 6-8 human donors at a concentration 10 μg/mL of CpG DNA. (B) Human B-cell proliferation requires the presence of a CpG stimulatory motif but not a secondary structure in DNA. Data shown are average±SD of 5-8 donors at a concentration of 1 μg/mL of CpG DNA.

Activation of human pDCs to induce IFN-α secretion by CpG DNAs 18, 19, 22, and 30 was studied. As seen in previous experiments, both 18 and 19 induced production of IFN-α (FIG. 15). Sequences 22, with a stimulatory motif but no secondary structure, and 30, with no stimulatory motif but with a secondary structure, failed to induce IFN-α production in pDC cultures (FIG. 15). These results suggest that both a stimulatory motif and a secondary structure in CpG DNAs were required for pDC activation.

The data for B-cell proliferation presented in FIG. 4B show that CpG DNAs 18 and 19, which formed secondary structures, and 22, which did not, induced strong B-cell proliferation. Sequence 30, which did not have a stimulatory motif, induced minimal proliferation, suggesting that a CpG motif was required for activity but a secondary structure was not.

Figure 16:
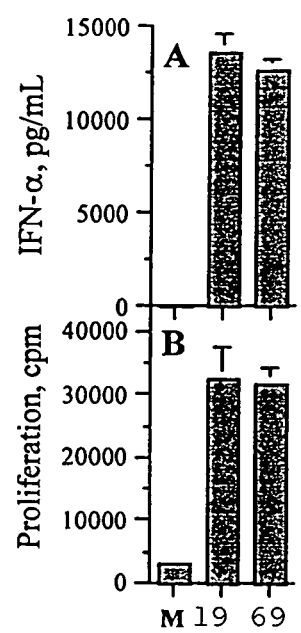
FIG. 16 Effect of 2'-O-methylribonucleotide segment in hairpin secondary structure on (A) IFN-α secretion by human pDCs and (B) human B-cell proliferation. Data shown are average±SD of 6-8 human donors at a concentration 10 μg/mL of CpG DNA in pDC cultures and 5-8 donors at a concentration of 1 μg/mL of CpG DNA in B cell cultures.

TLR9 specifically recognizes CpG DNA but not RNA. However, site-specific incorporation of 2'-O-alkylribonucleotides distal to the CpG dinucleotide in the flanking sequences is tolerated. We synthesized an analog of CpG DNA 19, in which the stem sequence close to the 3'-end, including the loop region, was replaced with 2'-O-methylribonucleotides. Both CpG DNAs 69 and 19 induced similar levels of IFN-α secretion in human pDC cultures (FIG. 16) and proliferation in human B-cell cultures (FIG. 16). These results suggested that 2'-O-methylribonucleotide substitutions or the conformational changes imposed by these substitutions did not interfere with either pDC or B-cell activation.

Toll-like receptor 9 (TLR9) recognizes unmethylated CpG DNA and activates several signaling pathways, including stress-kinase and NF-κB pathways, leading to the secretion of a number of chemokines and cytokines including IFN-α/β, IFN-γ, IL-12. IL-6, and TNF-α in vitro and in vivo. However, a direct interaction between CpG DNA and its receptor, TLR9, has not been established yet. The possible role of alternate receptors or co-receptors in CpG DNA immune stimulation has been proposed. CpG DNAs with different backbones, sequences, and structures activate the immune system in a cell-specific but TLR9-dependent fashion.

Optimal placement of a secondary structure at the 3'-end of CpG DNA could induce different cytokine profiles. CpG DNA structures with a human-specific motif induced high levels of IFN-α in human pDC cultures, suggesting that secondary structures may be required for pDC activation (unpublished data).

The present CpG DNAs were designed to contain two distinct domains, a stimulatory domain with a CpG-motif at the 5'-end and a structural domain containing sequences that permitted hairpin duplex formation at the 3'-end. The ability of these CpG DNAs to form intramolecular secondary structures provided additional stability against ubiquitous 3'-nucleases, hence the name self-stabilized CpG DNAs. Self-stabilized CpG DNAs differ from earlier reported palindromic CpG DNAs, which form intermolecular secondary structures and by not having CpG motifs in the structural domain region.

Palindromic sequences containing a CpG dinucleotide activate immune cells to produce IFN-α/β and -γ. The self-stabilized CpG DNAs described here allowed us to dissect the stimulatory and structural features of CpG DNA that were recognized by both human B cells and pDCs. CpG DNAs 18-21 activated pDCs in a hairpin duplex length-dependent fashion. Both control DNA molecules 22, with no structural domain, and 30, with no stimulatory domain, failed to induce IFN-α secretion, suggesting that both stimulatory and structural domains were required for pDC activation. On the contrary, B-cell activation required only the stimulatory domain and not the structural domain. The lower activity of CpG DNAs 20 and 21 suggested that secondary structures in CpG DNA may have interfered with B-cell activation. In fact, CpG DNA 30, which had no structural domain and was equal in nucleotide length to CpG DNA 18, activated B cells to a level equal to that of 19, suggesting that single-stranded DNAs were preferred for B-cell activation. The lower activation of B cells observed with 30 could be related to non-specific activity.

The present results with CpG DNA 69 suggested that the DNA/RNA hybrid heteroduplex did not impede either pDC or B cell activation. These results suggested that the B to A conformational changes imposed by the 2'-O-methylribonucleotide substitutions with in the structural domain region had little or no influence on immune stimulation, thus allowing substitutions at these positions In conclusion, in these studies we proposed a rational combination of stimulatory and structural domains in CpG DNAs for optimal activation of TLR9-positive subsets of human immune cells, pDCs and B cells. The studies presented here allowed us to determine the specific characteristics of CpG DNAs required for activation of pDCs and B cells. A CpG stimulatory motif was required for the activation of human B cells, while both the stimulatory motif and an additional structural domain were required for the activation of human pDCs. It is unclear why the same TLR9 receptor required different structural characteristics of its ligands for stimulation in two different cell populations. The fact that it did could indicate the involvement of different adapter molecules in TLR9 signaling in pDCs and B cells. The ability of self-stabilized CpG DNAs to activate both pDCs and B cells will permit the development of therapeutic agents for use against cancer, asthma, allergy, and infectious diseases and as adjuvant more potent than those that stimulate either B cells or pDCs.

TABLE 1

Schematic drawing[a], sequences, secondary structures and $T_m$s of CpG DNAs

| Number | Sequence (5'---->3')[b] | $T_m$, °C. |
|---|---|---|
| 18 | 1  TCGTCGTT-GAGCTCT G<br>                       CTCGAGA A<sup>A</sup> | 45.2 |

TABLE 1-continued

Schematic drawing[a], sequences, secondary structures and $T_m$s of CpG DNAs

Stimulatory domain | Structural domain

| Number | | Sequence (5'---->3')[b] | $T_m$, °C. |
|---|---|---|---|
| 19 | 2 | TCGTCGTT-GTGAGCTCTGT-G-A / CACTCGAGACA-A | 53.0 |
| 20 | 3 | TCGTCGTT-GCACAGAGCTCTGCT-G-A / CGTGTCTCGAGACGA-A | 68.7 |
| 21 | 4 | TCGTCGTT-GCTGACAGAGCTCTGCTAT-G-A / CGACTGTCTCGAGACGATA-A | 72.8 |
| 22 | 5 | TCGTCGTT-GTGCTCT-GAA-CTTGCTC | <8.0 |
| 30 | 6 | TGCTGCTT-GAGCTCT-G-A / CTCGAGA-A | 44.1 |
| 69 | 7 | TCGTCGTT-GTGAGCTCTGT-G-A / CA*CUC*GAGACA-A | 66.5 |
| 70 | 8 | GGTGCATCGATGCAGGGGGG GGGGGGACGTAGCTACGTGG | ND[c] |

[a]Schematic drawing of the novel CpG DNA design (box) showing the essential stimulatory and structural domains. The stimulatory domain, but not the structural domain, contained an appropriate CpG motif;
[b]All sequences are phosphorothioate modified except 8. Nucleotides shown in italic in 7 indicate 2'-O-methylribonucleotides, underlined nucleotides in 8 indicate phosphodiester backbone;
[c]ND-not determined.

The examples below are intended to further illustrate certain preferred embodiments of the invention, and are not intended to limit the scope of the invention.

EXAMPLES

Example 1

Oligonucleotide Synthesis, Purification and Thermal Melt Profiles

CpG oligos were synthesized on a 1 to 2 μmole scale using β-cyanoethylphosphoramidites on a PerSeptive Biosystem's 8909 Expedite DNA synthesizer (PerSeptive Biosystem, Boston, Mass.). The phosphoramidites of dA, dG, dC, and T were obtained from PE Biosystems (Foster City, Calif.). As described by Iyer R. P., et al. (*J. Am. Chem. Soc.* 112: 1253-1254 (1990)), an iodine oxidizing agent was used to obtain the phosphorothioate backbone modification. All oligos were deprotected using standard protocols, purified by HPLC, and dialyzed against USP quality sterile water for irrigation. The oligos were lyophilized and dissolved again in distilled water and the concentrations were determined from UV absorbance at 260 nm. All oligos were characterized by CGE and MALDI-TOF mass spectrometry (Applied Biosystem's Voyager-DE™ STR Biospectrometry™ Workstation) for purity and molecular mass, respectively. The purity of full-length oligos ranged from 90-96% with the rest being shorter by one or two nucleotides (n−1 and n−2) as determined by CGE and/or denaturing PAGE. All oligos contained less than <0.1 EU/mL of endotoxin as determined by the Limulus assay (Bio-Whittaker now known as Cambrex Bio Science Walkersville, Inc., Walkersville, Md.).

Thermal melting studies were carried out in 1 mL solution of 10 mM disodium hydrogen phosphate, pH 7.2±0.2, containing 150 mM NaCl, and 2 mM MgCl2. The solutions were heated to 95° C. for 10 min and allowed to come to room temperature slowly before being stored at 4° C. overnight. The final concentration of oligonucleotide strand was 2.0 μM. UV thermal melting measurements were performed at 260 nm on a Perkin-Elmer Lambda 20 Spectrophotometer attached to a peltier thermal controller and a personal computer using 1 cm path length quartz cuvettes at a heating rate of 0.5° C./min. Melting temperatures (Tm) were taken as the temperature of half-dissociation and were obtained from first derivative plots. Each Tm value is an average of two or three independent experiments and the values were within ±1.0° C.

A 17-mer phosphorothioate oligonucleotide (1) containing a 'GACGTT' hexameric motif was used as a positive control (Table 1). Oligonucleotides 2-7 contain additional sequences of five-, eleven-, or seventeen nucleotides complementary to parts of 1 (Table 1). Extensions are linked either at the 3'-(2-4) or 5'-end (5-7) and contain a GAA trimer that allows formation of a stable stem-loop as described by Hirao, I., et al. (*Nucleic Acids Res.* 22: 576-582 (1994)). Formation of hairpins by 2-7 was determined by UV thermal melting experiments. The Tm values of 40-66° C. in 10 mM sodium phosphate, pH 7.2, containing 150 mM NaCl, and 2 mM MgCl2 suggests that 2-7 formed stable secondary structures under the experimental conditions (Table 1). of interferon α (IFN-α) in plasmacytoid dendritic cells after exposure to oligos 18, 19, 20, and 21 at 10 μg/ml.

Example 2

Cell Culture Conditions and Reagents

Spleen cells from 4-8 week old BALB/c, C57BL/6 or C3H/HeJ mice were cultured in RPMI complete medium as described by Zhao, Q., et al. (*Biochem Pharmacol.* 51: 173-182 (1996)) and Branda, R. F., et al. (*Biochem. Pharmacol.* 45: 2037-2043 (1993)). Murine J774 macrophages (American Type Culture Collection, Manassas, Va.) were cultured in Dulbecco's modified Eagles medium supplemented with 10% (v/v) fetal calf serum and antibiotics (100 IU/mL of penicillin G/streptomycin). All other culture reagents were purchased from Mediatech (Gaithersburg, Md.).

Example 3

Spleen Cell Proliferation Assay

Typically, mouse (Balb-C) spleen cells were cultured with CpG oligos at concentrations of 0.1, 1.0, and 10.0 μg/ml for 48 h and cell proliferation was determined by 3H-uridine incorporation, as described by Zhao, Q., et al. (*Biochem Pharmacol.* 51: 173-182 (1996)).

Initially, oligos 1, 2, and 5 were examined for their ability to induce proliferation of BALB/c mouse spleen cells in cultures. Oligos 1 and 2 induced a dose-dependent spleen cell proliferation. The parent oligo 1, which did not have a stem-loop structure, showed a proliferation index of 6.0±0.3 at a concentration of 1.0 μg/mL (FIG. 1A). Oligo 2, which forms a stem-loop structure at its 3'-end gave a proliferation index of 9.0±2.5 at the same concentration. Oligo 5, which forms a stem-loop at its 5'-end, however, showed a lower proliferation index of 1.5±0.3 at the same concentration, which is similar to that of PBS control (FIG. 1A).

Example 4

Cytokine Induction Assays

Mouse spleen or J774 cells were plated in 24-well dishes using $5 \times 10^6$ or $1 \times 10^6$ cells/mL, respectively. The CpG oligos dissolved in TE buffer (10 mM Tris-HCl, pH 7.5, 1 mM EDTA) were added to a final concentration of 0.03, 0.1, 0.3, 1.0, 3.0, or 10.0 μg/mL to the cell cultures. The cells were then incubated at 37° C. for 24 hr and the supernatants were collected for ELISA assays. The experiments were performed two or three times for each CpG oligo and in triplicate for each concentration. The secretion of IL-12 and IL-6 was measured by sandwich ELISA as described by Bhagat L., et al. (*Biochem. Biophys. Res. Commun.* 300: 853-861 (2003)). The required reagents, including cytokine antibodies and standards were purchased from BD Biosciences Pharmingen (San Diego, Calif.).

Figure 2:
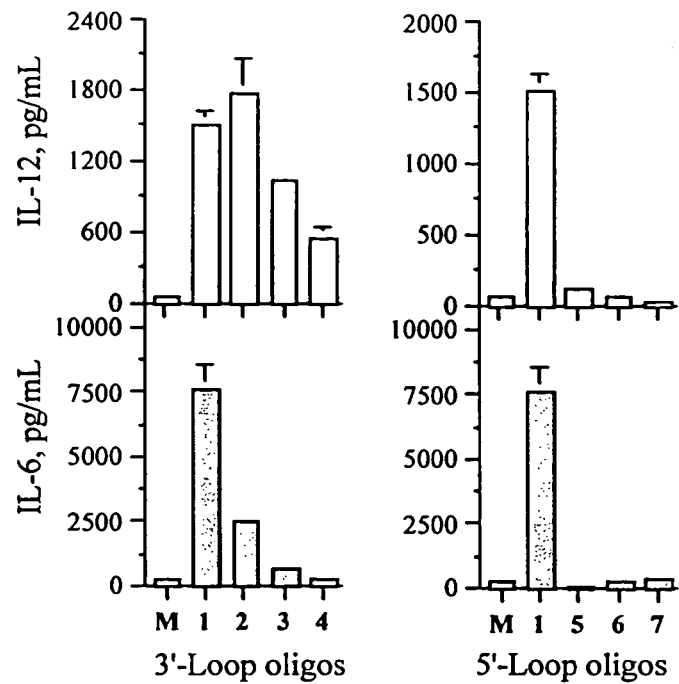
FIG. 2 is a schematic representation showing induction of cytokines IL-12 and IL-6 in BALB/c mouse spleen cell cultures after 24 hours of incubation with oligonucleotides 1-7 at a concentration of 3 µg/mL

CpG oligos induce a number of cytokines including IL-12 and IL-6. In BALB/c mouse spleen cell cultures test compounds 1 and 2 induced IL-12 and IL-6 by a concentration-dependent mechanism. Parent oligo 1 induced 1514±113 pg/mL of IL-12 and 7681±839 pg/mL of IL-6 at 3.0 μg/mL concentration (FIG. 2). Oligo 2, containing a 3'-hairpin, induced slightly more IL-12 (1771±286 pg/mL) and less IL-6 (2582±300 pg/mL). However, oligo 5, which has a 5'-hairpin, failed to induce cytokine secretion. These results suggest that a stable hairpin loop at the 5'-end, but not at the 3'-end, blocks immunostimulatory activity.

CpG DNAs 3 and 4 have 3'-hairpin stems that extend over the GACGTT motif or reach all the way to the 5'-end. As a result, they contain two CpG motifs, with GACGTT in the top strand and its complementary sequence, AACGTC in the bottom (Table 1). Oligos 6 and 7 have similarly long 5'-hairpins. Despite having two CpG motifs, oligos 3 and 4 induced lower IL-12 and minimal or no IL-6 compared with oligo 1 (FIG. 2). Both oligos 6 and 7, with 5'-hairpins, failed to induce cytokine secretion under the same experimental conditions. Minimal cytokine induction by oligo 4 suggests that the extension of stem structure to the 5'-end is detrimental and perhaps interferes with recognition and subsequent immune stimulation. These results suggest that a duplex stem structure extended to the 5' end interferes with immune stimulation.

Figure 3:
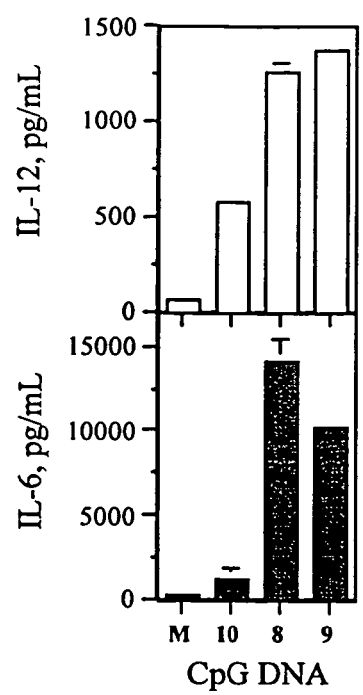
FIG. 3 is a schematic representation showing induction of cytokines IL-12 and IL-6 in BALB/c mouse spleen cell cultures after 24 hours of incubation with oligonucleotides 8-10 at a concentration of 3 µg/mL.

As base-pairing at the 5'-end of oligo 4 inhibited immune stimulation, duplex formation at both ends was investigated using CpG DNAs 8-10. Oligo 8 contains 18 nucleotides and the same GACGTT motif as oligo 1. Self-complementary 3'- or 5'-extensions in oligos 9 and 10 act as sticky ends to form dimers of eight base-pairs (Table 1). These duplexes contain phosphodiester linkages to reduce any length-dependent phosphorothioate effect on immune stimulation. Oligo 9 dimerizes at the 3'-end and showed similar IL-12 and IL-6 induction as its parent, oligo 8 (FIG. 3). However, oligo 10, which forms a 5'-duplex, induced minimal IL-12 and IL-6 (FIG. 3). Thus, the characteristic of forming a 5'-duplex strongly correlates with loss of immune stimulation. These results suggest that a duplex at the 5'- but not the 3'-end interferes with immunostimulation.

Figure 5:
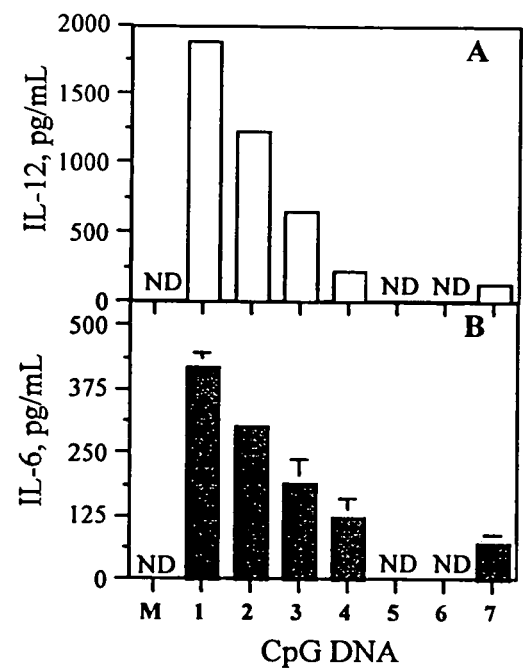
FIG. 5 is a schematic representation showing induction of cytokines IL-12 and IL-6 in J774 macrophage cell cultures at a concentration of oligos 1-7 of 10 µg/mL. M stands for control treated with PBS. ND denotes not detected.

The ability of oligos 1-7 to induce cytokine secretion in J774 cell cultures was also examined. The IL-12 and IL-6 data obtained at 10 μg/mL concentration of oligos (FIG. 5) complement the results obtained in splenocyte culture assays.

These results further confirm that the receptor reads the CpG DNA sequence from its 5'-end, and an accessible 5'-end is required for CpG DNA activity. The presence of secondary structures extending to the 5'-end in CpG oligos can interfere with receptor reading and thereby immunostimulatory activity.

Figure 6:
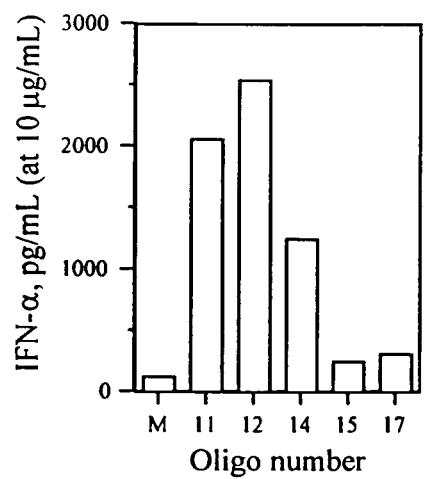
FIG. 6 is a schematic representation showing induction of interferon α (IFN-α) in plasmacytoid dendritic cells after exposure to oligos 11, 12, 14, 15 and 17 at 10 µg/ml.
Figure 7:
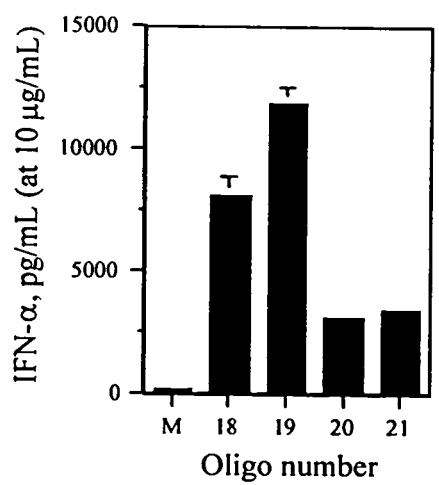
FIG. 7 is a schematic representation showing induction of interferon α (IFN-α) in plasmacytoid dendritic cells after exposure to oligos 18, 19, 20, and 21 at 10 µg/ml.
Figure 8:
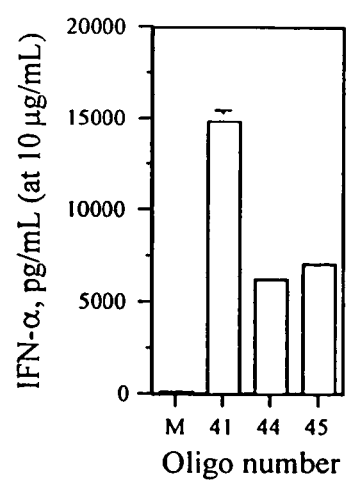
FIG. 8 is a schematic representation showing induction of interferon α (IFN-α) in plasmacytoid dendritic cells after exposure to oligos 41, 44, and 45 at 10 µg/ml.

The ability of oligonucleotides of the invention to induce the production of interferon α (INF-α) in plasmacytoid dendritic cells was also investigated. For the isolation and culturing of these cells see Krug, A., et al. (*Eur. J. Immmunol,* 31:2154-2163 (2001). Results are presented in FIGS. 6, 7 and 8. These data indicate that nucleic acid molecules of the invention with 3' hairpin structures stimulate the production of interferon-α, while 5'-end hairpin structures inhibit the immunostimulatory action, i.e., the production of intereon-α of these molecules.

Example 5

Mouse Splenomegaly Assay

Female BALB/c mice (4-6 weeks, 19-21 gm) were divided into groups of three mice. CpG oligos were dissolved in sterile phosphate buffered saline (PBS) and administered subcutaneously (SC) to mice at a dose of 5 mg/kg. The mice were sacrificed after 48 hr and the spleens were harvested and weighed as described by Zhao, Q., et al. (*Biochem Pharmacol.* 51: 173-182 (1996)) and Branda, R. F., et al. (*Biochem. Pharmacol.* 45: 2037-2043 (1993)).

Oligonucleotides 1, 2, and 5 were administered to BALB/c mice at a dose of 5 mg/kg to determine if they induce spleen enlargement in vivo. The increase in spleen weight in response to oligo treatment compared with the control group of mice injected with PBS is considered to be a result of immunostimulatory activity of CpG oligos (Zhao, Q., et al. *Biochem Pharmacol.* 51: 173-182 (1996); Branda, R. F., et al. *Biochem. Pharmacol.* 45: 2037-2043 (1993)). The results of in vivo studies are presented in FIG. 1B. Oligo 1, which did not have a stem-loop structure, and oligo 5, which had a stem-loop forming sequence at the 5'-end, increased spleen weight about 29% and 15%, respectively, compared with the control group that received PBS. In contrast, oligo 2, which had a stem-loop structure at the 3'-end, caused about 48% increase in spleen weight compared with the control group.

Example 6

Activation of the NF-κB Pathway

Toll-like receptor 9 (TLR9) has been shown to recognize unmethylated CpG-dinucleotides in bacterial, plasmid and synthetic DNAs (Hemmi H., et al. *Nature* 408: 740-745 (2000)) and activate stress kinase (Yi A. K., et al. *J. Immunol.* 161: 4493-4497 (1998)) and NF-κB pathways (Stacey K J., et al. *J. Immunol.* 157: 2116-2122 (1996)). NF-κB activation in J774 cells treated with CpG DNAs was carried out and analyzed by EMSA as described Yu D., et al. (*Biochem. Biophys. Res. Commun.* 297: 83-90 (2002)) and Bhagat L., et al. (*Biochem. Biophys. Res. Commun.* 300: 853-861 (2003)).

Figure 4:
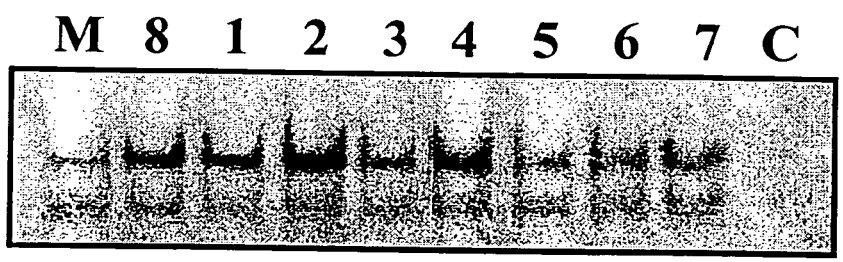
FIG. 4 is a representation showing activation of the NF-κB pathway in J774 macrophages after 1 hr stimulation with 10 µg/mL of oligos 1-8. M stands for control treated with media and C is cells treated with a non-CpG oligo.

The activation by oligos 1-7 of the NK-κB patheay in J774 was examined in murine macrophage cell nuclear extracts using EMSA. FIG. 4 shows the results obtained. Both parent oligos 1 and 8 activated NF-κB as indicated by the presence of a complex. Oligos 2-4, which have loop at the 3'-end, also activated NF-κB as indicated by the presence of the appropriate complex. In contrast, 5'-end loop oligos 5-7 failed to activate the transcription factor NF-κB in J774 cells (FIG. 4). A control non-CpG oligo failed to activate NF-kB under the same experimental conditions (lane C). These results are consistent with the data obtained in mouse spleen cell culture assays.

Example 7

Electrophoretic Mobility Shift Assay (EMSA)

About 0.2 OD of CpG DNAs and other markers were dissolved in 25 μL of 100 mM NaCl, 10 mM sodium phosphate, pH 7.2 buffer, heated to 90° C. for 15 min, allowed to come to room temperature and stored at 4° C. until analyzed on gel. The DNA samples prepared were mixed with glycerol buffer and resolved on a 15% non-denaturing polyacrylamide gel. The gel was visualized under 260 nm UV light.

Example 8

Isolation of Human B Cells and Plasmacytoid Dendritic Cells (pDCs)

PBMCs from freshly drawn healthy volunteer blood (CBR Laboratories, Boston, Mass.) were isolated by Ficoll density gradient centrifugation method (Histopaque-1077, Sigma) and B cells were isolated from PBMCs by positive selection using the CD19 cell isolation kit (Miltenyi Biotec) according to the manufacturer's instructions.

Example 9

B Cell Proliferation Assay

A total of $1\times10^5$ B cells/200 μl were stimulated with 0.3, 1.0, 3.0, or 10.0 μg/mL concentrations of CpG DNAs for 64 hr, then pulsed with 0.75 μCi of [$^3$H]-thymidine and harvested 8 h later. The incorporation of radioactivity was measured using liquid scintillation counter. Table 4 shows an average±SD of B cell proliferation for 6 CpG DNAs at a final concentration of 10.0 μg/mL.

TABLE 4

Immunomer Structure and Immunostimulatory Activity in Human B-Cell Proliferation Assay (72 hs)

| SEQ ID NO | Sequences and Modification (5'-3') | [$^3$H]-T (cpm) 10 μg/ml DN10 | [$^3$H]-T (cpm) 10 μg/ml DN11 |
|---|---|---|---|
| 60 | 5'-TCGTCGTT-GAGCUCU-G<br>                \|\|\|\|\|\|\| A<br>3'-CUCGAGA-A | 20317 ± 4825 | 25525 ± 6684 |
| 61 | 5'-TCGTCGTT-GAGCUCUCU-G<br>                \|\|\|\|\|\|\|\|\| A<br>3'-CUCGAGAGA-A | 8389 ± 5204 | 24895 ± 974 |
| 62 | 5'-TCGTCGTT-GAGCUCUCUGU-G<br>                \|\|\|\|\|\|\|\|\|\|\| A<br>3'-CUCGAGAGACA-A | 14804 ± 1262 | 22476 ± 3939 |
| 63 | 5'-TCRTCRTT-GTGAGCTCTGT-G<br>                \|\|\|\|\|\|\|\|\|\|\| A<br>3'-CACTCGAGACA-A | 13101 ± 7562 | 13965 ± 1396 |
| 64 and 71 | 5'-TCRTCRTT-X-GTGAGCTCTGT-G<br>                \|\|\|\|\|\|\|\|\|\|\| A<br>3'-CACTCGAGACA-A | 16893 ± 2870 | 14374 ± 3610 |
| 65 | 5'-TCRTCRTT-GTGAGCTCTGT-G<br>                \|\|\|\|\|\|\|\|\|\|\| A<br>3'-CACTCGAGACA-A | 15364 ± 1756 | 17197 ± 4625 |
| Media | | 1323 ± 511 | 2203 ± 804 |

Normal phase represents a phosphorothioate linkage; Underline represents a 2'-OMe ribonucleotide; X represents C3-linker.

Example 10

Human pDC Cultures and IFN-α ELISA pDCs were isolated from human PBMCs using a BDCA-4 cell isolation kit (Miltenyi Biotec) according to the manufacturer's instructions. pDC were plated in 96-well plates using $1\times10^6$ cells/mL, 200 μL/well). The oligonucleotides were added to a final concentration of 0.3, 1.0, 3.0, or 10.0 μg/mL to the cell cultures and incubated at 37° C. for 24 hr. Supernatants were then harvested and assayed for IFN-α IL-6 and IL-10 using ELISA kit (PBL). Tables 5A and 5B show an average±SD of IFN-α for 6 Oligonucleotides at a concentration of 10.0 μg/mL.

TABLE 5A

Immunomer Structure and Immunostimulatory Activity in Human Dendritic Cell Assay (24 hs)

| SEQ ID NO | Sequences and Modification (5'-3') | IFN-α(pg/ml) 10 µg/ml DN10 | IFN-α(pg/ml) 10 µg/ml DN11 | IFN-α(pg/ml) 10 µg/ml DN12 |
|---|---|---|---|---|
| 60 | 5'-TCGTCGTT-GAGCUCU-G<br>\|\|\|\|\|\|\| A<br>3'-CUCGAGA-A | 24895 ± 20 | 12520 ± 54 | 2358 ± 115 |
| 61 | 5'-TCGTCGTT-GAGCUCUCU-G<br>\|\|\|\|\|\|\|\|\| A<br>3'-CUCGAGAGA-A | 29911 ± 73 | 22622 ± 32 | 3239 ± 60 |
| 62 | 5'-TCGTCGTT-GAGCUCUCUGU-G<br>\|\|\|\|\|\|\|\|\|\| A<br>3'-CUCGAGAGACA-A | 28958 ± 475 | 26031 ± 188 | 7050 ± 584 |
| 63 | 5'-TCRTCRTT-GTGAGCTCTGT-G<br>\|\|\|\|\|\|\|\|\|\|\| A<br>3'-CACTCGAGACA-A | 11085 ± 0 | 22145 ± 0 | 1445 ± 0 |
| 64 and 71 | 5'-TCRTCRTT-X-GTGAGCTCTGT-G<br>\|\|\|\|\|\|\|\|\|\|\| A<br>3'-CACTCGAGACA-A | 136675 ± 0 | 106575 ± 0 | 29605 ± 0 |
| 65 | 5'-TCRTCRTT-GTGAGCTCTGT-G<br>\|\|\|\|\|\|\|\|\|\|\| A<br>3'-CACUCGAGACA-A | 1 ± 0 | 2 ± 0 | 376 ± 5 |

| SEQ ID NO | Sequences and Modification (5'-3') | IFN-α(pg/ml) 10 µg/ml DN1 | IFN-α(pg/ml) 10 µg/ml DN2 | IFN-α(pg/ml) 10 µg/ml DN3 |
|---|---|---|---|---|
| 64 and 71 | 5'-TCRTCRTT-X-GTGAGCTCTGT-G<br>\|\|\|\|\|\|\|\|\|\|\| A<br>3'-CACTCGAGACA-A | | | |
| 64 and 47 | 5'-TCRTCRTT-XXX-GTCTCGAGAC-5' | 38172 ± 428 | 53584 ± 217 | 18470 ± 131 |
| 64 and 72 | 5'-TCRTCRTT-XXX-GUCUCGAGAC-5' | 55684 ± 579 | 56332 ± 337 | 32858 ± 143 |
| media | | 0 ± 0 | 546 ± 0 | 160 ± 7 |

| SEQ ID NO | Sequences and Modification (5'-3') | IFN-α(pg/ml) 10 µg/ml DN4 | IFN-α(pg/ml) 10 µg/ml DN5 | IFN-α(pg/ml) 10 µg/ml DN6 |
|---|---|---|---|---|
| 64 and 71 | 5'-TCRTCRTT-X-GTGAGCTCTGT-G<br>\|\|\|\|\|\|\|\|\|\|\| A<br>3'-CACTCGAGACA-A | | 18430 ± 81 | 47712 ± 157 |
| 64 and 47 | 5'-TCRTCRTT-XXX-GTCTCGAGAC-5' | 25616 ± 1056 | 16352 ± 102 | 45168 ± 281 |
| 64 and 72 | 5'-TCRTCRTT-XXX-GUCUCGAGAC-5' | 28346 ± 1621 | | |
| media | | 259 ± 20 | 1590 ± 8 | 226 ± 7 |

| SEQ ID NO | Sequences and Modification (5'-3') | IFN-α(pg/ml) 10 µg/ml DN7 | IFN-α(pg/ml) 10 µg/ml DN8 | IFN-α(pg/ml) 10 µg/ml DN9 |
|---|---|---|---|---|
| 64 and 71 | 5'-TCRTCRTT-X-GTGAGCTCTGT-G<br>\|\|\|\|\|\|\|\|\|\|\| A<br>3'-CACTCGAGACA-A | 1275 ± 179 | 46380 ± 894 | 55932 ± 133 |
| 64 and 47 | 5'-TCRTCRTT-XXX-GTCTCGAGAC-5' | 2080 ± 287 | | |
| 64 and 72 | 5'-TCRTCRTT-XXX-GUCUCGAGAC-5' | | | |
| media | | 389 ± 38 | 0 ± 0 | 0 ± 0 |

TABLE 5A-continued

Immunomer Structure and Immunostimulatory Activity in Human Dendritic Cell Assay (24 hs)

| SEQ ID NO | Sequences and Modification (5'-3') | IFN-α(pg/ml) 10 µg/ml DN10 | IFN-α(pg/ml) 10 µg/ml DN11 | |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 53640 ± 1044 | 91325 ± 388 | |
| 64 and 47 | 5'-TCRTCRTT-XXX-GTCTCGAGAC-5' | | | |
| 64 and 72 | 5'-TCRTCRTT-XXX-GUCUCGAGAC-5' | | | |
| media | | 218 ± 6 | 218 ± 0 | |

| SEQ ID NO | Sequences and Modification (5'-3') | IL-6(pg/ml) 10 µg/ml DN5 | IL-6(pg/ml) 10 µg/ml DN6 | IL-6(pg/ml) 10 µg/ml DN7 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 1185 ± 42 | 2569 ± 57 | 2132 ± 22 |
| 64 and 47 | 5'-TCRTCRTT-XXX-GTCTCGAGAC-5' | 4003 ± 88 | 5716 ± 30 | 4218 ± 41 |
| 64 and 72 | 5'-TCRTCRTT-XXX-GUCUCGAGAC-5' | | | |
| media | | 180 ± 6 | 1008 ± 19 | 693 ± 0 |

| SEQ ID NO | Sequences and Modification (5'-3') | IL-6(pg/ml) 10 µg/ml DN8 | IL-6(pg/ml) 10 µg/ml DN9 | IL-6(pg/ml) 10 µg/ml DN10 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 9320 ± 104 | 9356 ± 4 | 16362 ± 244 |
| 64 and 47 | 5'-TCRTCRTT-XXX-GTCTCGAGAC-5' | | | |
| 64 and 72 | 5'-TCRTCRTT-XXX-GUCUCGAGAC-5' | | | |
| media | | 1221 ± 14 | 1221 ± 20 | 517 ± 0 |

| SEQ ID NO | Sequences and Modification (5'-3') | IL-10(pg/ml) 10 µg/ml DN5 | IL-10(pg/ml) 10 µg/ml DN6 | IL-10(pg/ml) 10 µg/ml DN7 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 225 ± 12 | 277 ± 22 | 238 ± 13 |
| 64 and 47 | 5'-TCRTCRTT-XXX-GTCTCGAGAC-5' | 935 ± 18 | 2455 ± 256 | 1507 ± 83 |
| 64 and 72 | 5'-TCRTCRTT-XXX-GUCUCGAGAC-5' | | | |
| media | | 228 ± 4 | 200 ± 17 | 104 ± 5 |

| SEQ ID NO | Sequences and Modification (5'-3') | IL-10(pg/ml) 10 µg/ml DN8 | IL-10(pg/ml) 10 µg/ml DN9 | IL-10(pg/ml) 10 µg/ml DN10 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 3135 ± 101 | 5418 ± 138 | 1283 ± 135 |
| 64 and 47 | 5'-TCRTCRTT-XXX-GTCTCGAGAC-5' | | | |
| 64 and 72 | 5'-TCRTCRTT-XXX-GUCUCGAGAC-5' | | | |
| media | | 913 ± 14 | 913 ± 14 | 0 ± 0 |

Normal phase represents a phosphorothioate linkage; Underline represents a 2'-OMe ribonucleotide; X represents C3-linker R = 2'-deoxy-7-deazaguanosine

TABLE 5B

Immunomer Structure and Immunostimulatory Activity in Human Dendritic Cell Assay (24 hs)

| SEQ ID NO | Sequences and Modification (5'-3') | IFN-α(pg/ml) 10 µg/ml DN1 | IFN-α(pg/ml) 10 pg/ml DN2 | IFN-α(pg/ml) 10 pg/ml DN3 |
|---|---|---|---|---|
| 64 and 71 | 5'-TCRTCRTT-X-GTGAGCTCTGT-G<br>\|\|\|\|\|\|\|\|\|\|\| \A<br>3'-CACTCGAGACA-A / | 4473 ± 222 | 9424 ± 194 | 6342 ± 15 |
| 65 | 5'-TCRTCRTT-GTGAGCTCTGT-G<br>\|\|\|\|\|\|\|\|\|\|\| \A<br>3'-CACUCGAGACA-A / | 9105 ± 493 | 13768 ± 33 | 6285 ± 19 |
| 64 and 73 | 5'-TCRTCRTT-X-GUGAGCUCUGU-G<br>\|\|\|\|\|\|\|\|\|\|\| \A<br>3'-CACUCGAGACA-A / | 2138 ± 96 | 9004 ± 130 | 5225 ± 32 |
| Media | | 0 ± 0 | 0 ± 0 | 0 ± 0 |

| SEQ ID NO | Sequences and Modification (5'-3') | IFN-α(pg/ml) 10 µg/ml DN4 | IFN-α(pg/ml) 10 pg/ml DN5 | IFN-α(pg/ml) 10 pg/ml DN6 |
|---|---|---|---|---|
| 64 and 71 | 5'-TCRTCRTT-X-GTGAGCTCTGT-G<br>\|\|\|\|\|\|\|\|\|\|\| \A<br>3'-CACTCGAGACA-A / | 5297 ± 70 | 12240 ± 905 | 68215 ± 1723 |
| 65 | 5'-TCRTCRTT-GTGAGCTCTGT-G<br>\|\|\|\|\|\|\|\|\|\|\| \A<br>3'-CACUCGAGACA-A / | 5646 ± 4 | 14092 ± 1011 | 87225 ± 717 |
| 64 and 73 | 5'-TCRTCRTT-X-GUGAGCUCUGU-G<br>\|\|\|\|\|\|\|\|\|\|\| \A<br>3'-CACUCGAGACA-A / | 0 ± 0 | 17135 ± 968 | 106554 ± 1319 |
| Media | | 0 ± 0 | 152 ± 0 | 181 ± 5 |

Normal phase represents a phosphorothioate linkage; Underline = 2'-OMe-nucleoside; R = 2'-deoxy-7-deazaguanosine; X = C3-linker

| SEQ ID NO | Sequences and Modification (5'-3') | IFN-α(pg/ml) 10 µg/ml DN1 | IFN-α(pg/ml) 10 pg/ml DN2 | IFN-α(pg/ml) 10 pg/ml DN3 |
|---|---|---|---|---|
| 66 and 74 | 5'-TCG₁TCG₁TT-XXX-_GUCUCGAGAC_-5' | 3618 ± 0 | 3590 ± 136 | 5507 ± 93 |
| 66 and 75 | 5'-TCG₁TCG₁TT-XXX-GTCTCCACTC-5' | 728 ± 71 | 1822 ± 54 | 5386 ± 0 |
| 66 and 76 | 5'-TCG₁TCG₁TT-XXX-_GUCUCCACUC_-5' | 0 ± 0 | 678 ± 0 | 0 ± 0 |
| 66 and 47 | 5'-TCG₁TCG₁TT-XXX-GTCTCGAGAC-5' | 5922 ± 187 | 16662 ± 285 | 5924 ± 11 |
| 66 and 72 | 5'-TCG₁TCG₁TT-XXX-_GUCUCGAGAC_-5' | 9606 ± 298 | 27240 ± 165 | 6380 ± 2 |
| Media | | 0 ± 0 | 0 ± 0 | 0 ± 0 |

| SEQ ID NO | Sequences and Modification (5'-3') | IFN-α(pg/ml) 10 µg/ml DN4 | IFN-α(pg/ml) 10 pg/ml DN5 | IFN-α(pg/ml) 10 pg/ml DN6 |
|---|---|---|---|---|
| 66 and 74 | 5'-TCG₁TCG₁TT-XXX-_GUCUCGAGAC_-5' | 5018 ± 41 | 19654 ± 1137 | 1000 ± 26 |
| 66 and 75 | 5'-TCG₁TCG₁TT-XXX-GTCTCCACTC-5' | 665 ± 87 | 181 ± 2 | 457 ± 23 |
| 66 and 76 | 5'-TCG₁TCG₁TT-XXX-_GUCUCCACUC_-5' | 2557 ± 663 | 807 ± 149 | 220 ± 31 |
| 66 and 47 | 5'-TCG₁TCG₁TT-XXX-GTCTCGAGAC-5' | 59344 ± 293 | 845 ± 60 | 1579 ± 83 |

TABLE 5B-continued

Immunomer Structure and Immunostimulatory Activity in Human Dendritic Cell Assay (24 hs)

| | | | | |
|---|---|---|---|---|
| 66 and 72 | 5'-TCG₁TCG₁TT-XXX-*GUCUCGAGAC*-5' | 89595 ± 1421 | 12088 ± 322 | 2292 ± 83 |
| Media | | 152 ± 0 | 181 ± 5 | 110 ± 0 |

Normal phase represents a phosphorothioate linkage; Italic phase represents a phosphodiester linkage.
Underline = 2'-OMe-nucleoside
R = 2'-deoxy-7-deazaguanosine  G₁ = 2'-deoxy-7-deazaguanoise
X = Glycerol linker

Example 11

Cytokine Analysis

The secretion of IFN-2 and IL-6 in vertebrate cells, preferably BALB/c mouse spleen cells or human PBMC, was measured by sandwich ELISA. The required reagents including cytokine antibodies and cytokine standards were purchased form PharMingen, San Diego, Calif. ELISA plates (Costar) were incubated with appropriate antibodies at 5 μg/mL in PBSN buffer (PBS/0.05% sodium azide, pH 9.6) overnight at 4° C. and then blocked with PBS/1% BSA at 37° C. for 30 minutes. Cell culture supernatants and cytokine standards were appropriately diluted with PBS/10% FBS, added to the plates in triplicate, and incubated at 25° C. for 2 hours. Plates were overlaid with 1 μg/mL appropriate biotinylated antibody and incubated at 25° C. for 1.5 hours. The plates were then washed extensively with PBS-T Buffer (PBS/0.05% Tween 20) and further incubated at 25° C. for 1.5 hours after adding streptavidin conjugated peroxidase (Sigma, St. Louis, Mo.). The plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments).

Human peripheral blood mononuclear cells (PBMCs) were isolated from peripheral blood of healthy volunteers by Ficoll-Paque density gradient centrifugation (Histopaque-1077, Sigma, St. Louis, Mo.). Briefly, heparinized blood was layered onto the Histopaque-1077 (equal volume) in a conical centrifuge and centrifuged at 400×g for 30 minutes at room temperature. The buffy coat, containing the mononuclear cells, was removed carefully and washed twice with isotonic phosphate buffered saline (PBS) by centrifugation at 250×g for 10 minutes. The resulting cell pellet was then resuspended in RPMI 1640 medium containing L-glutamine (MediaTech, Inc., Herndon, Va.) and supplemented with 10% heat inactivated FCS and penicillin-streptomycin (100 U/ml). Cells were cultured in 24 well plates for different time periods at 1×10⁶ cells/ml/well in the presence or absence of oligonucleotides. At the end of the incubation period, supernatants were harvested and stored frozen at −70° C. until assayed for various cytokines including IL-6 (BD Pharmingen, San Diego, Calif.), and IFN-α (BioSource International) by sandwich ELISA. The results are shown in Table 6A and 6B below.

In all instances, the levels of IFN-2 and IL-6 in the cell culture supernatants was calculated from the standard curve constructed under the same experimental conditions for IFN-2 and IL-6 respectively.

TABLE 6A

Immunomer Structure and Immunostimulatory Activity in Human PBMC Assay (24 hs)

| SEQ ID NO | Sequences and Modification (5'-3') | IL-6 (pg/ml) 10 μg/ml DN1 | IL-6 (pg/ml) 10 μg/ml DN2 | IL-6 (pg/ml) 10 μg/ml DN3 |
|---|---|---|---|---|
| 64 and 71 | 5'-TCRTCRTT-X-GTGAGCTCTGT-G⧹<br>              \|\|\|\|\|\|\|\|\|\|\| A<br>3'-CACTCGAGACA-A⧸ | 1086 ± 10 | 683 ± 3 | 1981 ± 60 |
| 64 and 47 | 5'-TCRTCRTT-XXX-GTCTCGAGAC-5' | 2480 ± 87 | 5606 ± 246 | 3412 ± 265 |
| 64 and 72 | 5'-TCRTCRTT-XXX-*GUCUCGAGAC*-5' | | | |
| media | | 318 ± 10 | 292 ± 9 | 364 ± 7 |
| SEQ ID NO | Sequences and Modification (5'-3') | IL-6 (pg/ml) 10 μg/ml DN8 | IL-6 (pg/ml) 10 μg/ml DN9 | IL-6 (pg/ml) 10 μg/ml DN10 |
| 64 and 71 | 5'-TCRTCRTT-X-GTGAGCTCTGT-G⧹<br>              \|\|\|\|\|\|\|\|\|\|\| A<br>3'-CACTCGAGACA-A⧸ | 1375 ± 7 | 599 ± 3 | 331 ± 17 |

TABLE 6A-continued

Immunomer Structure and Immunostimulatory Activity in Human PBMC Assay (24 hs)

| | | | | |
|---|---|---|---|---|
| 64 and 47 | 5'-TCRTCRTT-XXX-GTCTCGAGAC-5' | | | |
| 64 and 72 | 5'-TCRTCRTT-XXX-<u>GUCUCGAGAC</u>-5' | | | |
| media | | 77 ± 3 | 0 ± 0 | nd |

Normal phase represents a phosphorothioate linkage; Underline represents a 2'-OMe ribonucleotide; X represents C3-linker
R = 2'-deoxy-7-deazaguanosine

TABLE 6B

Immunomer Structure and Immunostimulatory Activity in Human PBMC Assay (24 hs)

| SEQ ID NO | Sequences and Modification (5'-3') | IFN-α(pg/ml) 10 µg/ml DN1 | IFN-α(pg/ml) 10 µg/ml DN2 | IFN-α(pg/ml) 10 µg/ml DN3 |
|---|---|---|---|---|
| 64 and 71 | 5'-TCRTCRTT-X-GTGAGCTCTGT-G\\<br>\|\|\|\|\|\|\|\|\|\|\|     A<br>3'-CACTCGAGACA-A/ | 19 ± 11 | 12 ± 1 | 9 ± 0 |
| 65 | 5'-TCRTCRTT-GTGAGCTCTGT-G\\<br>\|\|\|\|\|\|\|\|\|\|\|     A<br>3'-<u>CACUCGAGACA</u>-A/ | 7 ± 1 | 31 ± 0 | 8 ± 0 |
| 64 and 73 | 5'-TCRTCRTT-X-<u>GUGAGCUCUGU</u>-G\\<br>\|\|\|\|\|\|\|\|\|\|\|     A<br>3'-<u>CACUCGAGACA</u>-A/ | 29 ± 3 | 20 ± 3 | 8 ± 0 |
| Media | | 0 ± 0 | 0 ± 0 | 0 ± 0 |

| SEQ ID NO | Sequences and Modification (5'-3') | IFN-α(pg/ml) 10 µg/ml DN4 | IFN-α(pg/ml) 10 µg/ml DN5 | IFN-α(pg/ml) 10 µg/ml DN6 |
|---|---|---|---|---|
| 64 and 71 | 5'-TCRTCRTT-X-GTGAGCTCTGT-G\\<br>\|\|\|\|\|\|\|\|\|\|\|     A<br>3'-CACTCGAGACA-A/ | 9 ± 0 | 23 ± 0 | 10 ± 0 |
| 65 | 5'-TCRTCRTT-GTGAGCTCTGT-G\\<br>\|\|\|\|\|\|\|\|\|\|\|     A<br>3'-<u>CACUCGAGACA</u>-A/ | 8 ± 0 | 17 ± 1 | 12 ± 1 |
| 64 and 73 | 5'-TCRTCRTT-X-<u>GUGAGCUCUGU</u>-G\\<br>\|\|\|\|\|\|\|\|\|\|\|     A<br>3'-<u>CACUCGAGACA</u>-A/ | 8 ± 0 | 12 ± 1 | 10 ± 0 |
| Media | | 0 ± 0 | 11 ± 1 | 10 ± 0 |

Normal phase represents a phosphorothioate linkage; Underline = 2'-OMe-nucleoside; R = 2'-deoxy-7-deazaguanosine; X = C3-linker

| SEQ ID NO | Sequences and Modification (5'-3') | IFN-α(pg/ml) 10 µg/ml DN1 | IFN-α(pg/ml) 10 µg/ml DN2 | IFN-α(pg/ml) 10 µg/ml DN3 |
|---|---|---|---|---|
| 66 and 74 | 5'-TCG₁TCG₁TT-XXX-<u>GUCUCGAGAC</u>-5' | 4 ± 1 | 8 ± 1 | 9 ± 0 |
| 66 and 75 | 5'-TCG₁TCG₁TT-XXX-GTCTCCACTC-5' | 7 ± 0 | 3 ± 0 | 9 ± 0 |
| 66 and 76 | 5'-TCG₁TCG₁TT-XXX-<u>GUCUCCACUC</u>-5' | 2 ± 0 | 9 ± 0 | 8 ± 0 |
| 66 and 47 | 5'-TCG₁TCG₁TT-XXX-GTCTCGAGAC-5' | 3 ± 1 | 6 ± 1 | 9 ± 0 |
| 66 and 72 | 5'-TCG₁TCG₁TT-XXX-<u>GUCUCGAGAC</u>-5' | 18 ± 2 | 11 ± 1 | 9 ± 0 |

TABLE 6B-continued

Immunomer Structure and Immunostimulatory Activity in Human PBMC Assay (24 hs)

| | | | | |
|---|---|---|---|---|
| Media | | 0 ± 0 | 0 ± 0 | 0 ± 0 |
| SEQ ID NO | Sequences and Modification (5'-3') | IFN-α(pg/ml) 10 µg/ml DN4 | IFN-α(pg/ml) 10 µg/ml DN5 | IFN-α(pg/ml) 10 µg/ml DN6 |
| 66 and 74 | 5'-TCG₁TCG₁TT-XXX-*GUCUCGAGAC*-5' | 18 ± 1 | 74 ± 5 | 5 ± 0 |
| 66 and 75 | 5'-TCG₁TCG₁TT-XXX-GTCTCCACTC-5' | 16 ± 0 | 11 ± 0 | 17 ± 2 |
| 66 and 76 | 5'-TCG₁TCG₁TT-XXX-*GUCUCCACUC*-5' | 11 ± 0 | 11 ± 0 | 17 ± 0 |
| 66 and 47 | 5'-TCG₁TCG₁TT-XXX-GTCTCGAGAC-5' | 35 ± 1 | 14 ± 1 | 52 ± 7 |
| 66 and 72 | 5'-TCG₁TCG₁TT-XXX-*GUCUCGAGAC*-5' | 86 ± 9 | 53 ± 8 | 13 ± 2 |
| Media | | 11 ± 1 | 10 ± 0 | 6 ± 1 |

Normal phase represents a phosphorothioate linkage; Italic phase represents a phosphodiester linkage; Underline = 2'-OMe-nucleoside R = 2'-deoxy-7-deazaguanosine G₁ = 2'-deoxy-7-deazaguanoise
X = Glycerol linker Example 12

B Cell Assay

B-Cells were plated in 96-well plates using 1×10⁶ cells/mL, 200 µL/well). The Oligonucleotides were added to a final concentration of 0.3, 1.0, 3.0, or 10.0 µg/mL to the cell cultures and incubated at 37° C. for 24 hr. Supernatants were then harvested and assayed for IL-6 using ELISA kit (provided by PBL). Table 7 show an average±SD for Donors 5-10 with oligonucleotides at a final concentration of 10.0 µg/mL.

Flow Cytometric Analysis

Cell surface markers of CD69 and CD86 were detected with a Coulter Epics-XL Flow Cytometer using anti-human CD69-Fitc and CD86-Fitc, which were purchased from BD Pharmingen (San Diego, USA). Staining methods were briefly descried as follow. The activated culture cells were blocked with 10% Human AB serum (Sigma) in staining buffer (PBS with 1% BSA and 0.1% NaN₃) at 4° C. for 1 hour and stained with the antibodies at 4° C. overnight. PBMCs (4×10⁵) were stained with CD69-Fitc and CD86-Fitc. PDCs (2×10⁵) were stained CD86-Fitc. The cell staining data were acquired and analyzed with Coulter System II software.

TABLE 7

Immunomer Structure and Immunostimulatory Activity in Human B-Cell Assay (24 hs)

| SEQ ID NO | Sequences and Modification (5'-3') | IL-6(pg/ml) 10 µg/ml DN5 | IL-6(pg/ml) 10 µg/ml DN6 | IL-6(pg/ml) 10 µg/ml DN7 |
|---|---|---|---|---|
| 64 and 71 | 5'-TCRTCRTT-X-GTGAGCTCTGT-G<br>           \|\|\|\|\|\|\|\|\|\|\| A<br>3'-CACTCGAGACA-A | 808 ± 60 | 231 ± 6.3 | 1483 ± 232 |
| 64 and 47 | 5'-TCRTCRTT-XXX-GTCTCGAGAC-5' | 1317 ± 70 | 1374 ± 30 | 2385 ± 157 |
| 64 and 72 | 5'-TCRTCRTT-XXX-*GUCUCGAGAC*-5' | | | |
| media | | 72 ± 0.9 | 342 ± 18 | 460 ± 0.8 |
| SEQ ID NO | Sequences and Modification (5'-3') | IL-6(pg/ml) 10 µg/ml DN8 | IL-6(pg/ml) 10 µg/ml DN9 | IL-6(pg/ml) 10 µg/ml DN10 |
| 64 and 71 | 5'-TCRTCRTT-X-GTGAGCTCTGT-G<br>           \|\|\|\|\|\|\|\|\|\|\| A<br>3'-CACTCGAGACA-A | 1061 ± 3.4 | 609 ± 1.8 | 98 ± 8 |
| 64 and 47 | 5'-TCRTCRTT-XXX-GTCTCGAGAC-5' | | | |
| 64 and 72 | 5'-TCRTCRTT-XXX-*GUCUCGAGAC*-5' | | | |
| media | | 68 ± 11 | 284 ± 3 | 10 ± 0.7 |

Normal phase represents a phosphorothioate linkage; Underline represents a 2'-OMe ribonucleotide; X represents C3-linker
R = 2'-deoxy-7-deazaguanosine

TABLE 8

Immunomer Structure and Expression of BC from Human PBMC (24 hs)

| SEQ ID NO | Sequences and Modification (5'-3') | % CD86 1 μg/ml DN1 | % CD86 1 μg/ml DN2 | % CD86 1 μg/ml DN3 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 23.8 | 28.6 | 27.7 |
| 65 | 5'-TCRTCRTT-GTGAGCTCTGT-G\<br>\|\|\|\|\|\|\|\|\|\|\| A<br>3'-<u>CACUCGAGACA</u>-A/ | 23.4 | 25 | 22 |
| 64 and 73 | 5'-TCRTCRTT-X-<u>GUGAGCUCUGU</u>-G\<br>\|\|\|\|\|\|\|\|\|\|\| A<br>3'-<u>CACUCGAGACA</u>-A/ | 17.6 | 22.9 | 17.9 |
| Media | | 16.4 | 17.3 | 17.3 |

| SEQ ID NO | Sequences and Modification (5'-3') | % CD86 1 μg/ml DN4 | % CD86 1 μg/ml DN5 | % CD86 1 μg/ml DN6 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 16.2 | 28.4 | 11.4 |
| 65 | 5'-TCRTCRTT-GTGAGCTCTGT-G\<br>\|\|\|\|\|\|\|\|\|\|\| A<br>3'-<u>CACUCGAGACA</u>-A/ | 15.9 | 29.1 | 13.5 |
| 64 and 73 | 5'-TCRTCRTT-X-<u>GUGAGCUCUGU</u>-G\<br>\|\|\|\|\|\|\|\|\|\|\| A<br>3'-<u>CACUCGAGACA</u>-A/ | 15.7 | 27.6 | 10.2 |
| Media | | 20.5 | 25.7 | 12.5 |

| SEQ ID NO | Sequences and Modification (5'-3') | % CD69 1 μg/ml DN1 | % CD69 1 μg/ml DN2 | % CD69 1 μg/ml DN3 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 11.3 | 22.2 | 24.5 |
| 65 | 5'-TCRTCRTT-GTGAGCTCTGT-G\<br>\|\|\|\|\|\|\|\|\|\|\| A<br>3'-<u>CACUCGAGACA</u>-A/ | 9.2 | 18.8 | 12.3 |
| 64 and 73 | 5'-TCRTCRTT-X-<u>GUGAGCUCUGU</u>-G\<br>\|\|\|\|\|\|\|\|\|\|\| A<br>3'-<u>CACUCGAGACA</u>-A/ | 8.3 | 22.2 | 17.8 |
| Media | | 5.9 | 11.5 | 12 |

| SEQ ID NO | Sequences and Modification (5'-3') | % CD69 1 μg/ml DN4 | % CD69 1 μg/ml DN5 | % CD69 1 μg/ml DN6 |
|---|---|---|---|---|
| 64 and 71 | 5'-TCRTCRTT-X-GTGAGCTCTGT-G\<br>\|\|\|\|\|\|\|\|\|\|\| A<br>3'-CACTCGAGACA-A/ | 8.8 | 8 | 15.1 |
| 65 | 5'-TCRTCRTT-GTGAGCTCTGT-G\<br>\|\|\|\|\|\|\|\|\|\|\| A<br>3'-<u>CACTCGAGACA</u>-A/ | 8.1 | 14.4 | 13.5 |
| 64 and 73 | 5'-TCRTCRTT-X-<u>GUGAGCUCUGU</u>-G\<br>\|\|\|\|\|\|\|\|\|\|\| A<br>3'-<u>CACUCGAGACA</u>-A/ | 6.6 | 9 | 11.4 |
| Media | | 7.6 | 5.4 | 10.2 |

Normal phase represents a phosphorothioate linkage; Underline = 2'-OMe-nucleoside; R = 2'-deoxy-7-deazaguanosine; X = C3-linker TABLE 8-continued Immunomer Structure and Expression of BC from Human PBMC (24 hs)

| SEQ ID NO | Sequences and Modification (5'-3') | % CD86 1 μg/ml DN1 | % CD86 1 μg/ml DN2 | % CD86 1 μg/ml DN3 |
|---|---|---|---|---|
| 66 and 74 | 5'-TCG₁TCG₁TT-XXX-*GUCUCGAGAC*-5' | 19.8 | 14 | 29.2 |
| 66 and 75 | 5'-TCG₁TCG₁TT-XXX-GTCTCCACTC-5' | 52.5 | 45 | 42.3 |
| 66 and 76 | 5'-TCG₁TCG₁TT-XXX-*GUCUCCACUC*-5' | 27.5 | 22.2 | 23.6 |
| 66 and 47 | 5'-TCG₁TCG₁TT-XXX-GTCTCGAGAC-5' | 42.6 | 43.5 | 33.3 |
| 66 and 72 | 5'-TCG₁TCG₁TT-XXX-*GUCUCGAGAC*-5' | 21.9 | 25.4 | 17 |
| Media | | 16.4 | 17.3 | 20.5 |

| SEQ ID NO | Sequences and Modification (5'-3') | % CD86 1 μg/ml DN4 | % CD86 1 μg/ml DN5 | % CD86 1 μg/ml DN6 |
|---|---|---|---|---|
| 66 and 74 | 5'-TCG₁TCG₁TT-XXX-*GUCUCGAGAC*-5' | 24.6 | 9.5 | 27.9 |
| 66 and 75 | 5'-TCG₁TCG₁TT-XXX-GTCTCCACTC-5' | 29.6 | 17.1 | 52.5 |
| 66 and 76 | 5'-TCG₁TCG₁TT-XXX-*GUCUCCACUC*-5' | 25 | 17.5 | 27.7 |
| 66 and 47 | 5'-TCG₁TCG₁TT-XXX-GTCTCGAGAC-5' | 34.7 | 10.7 | 43.5 |
| 66 and 72 | 5'-TCG₁TCG₁TT-XXX-*GUCUCGAGAC*-5' | 27.5 | 7.1 | 27 |
| Media | | 25.7 | 12.5 | 28.8 |

| SEQ ID NO | Sequences and Modification (5'-3') | % CD69 1 μg/ml DN1 | % CD69 1 μg/ml DN2 | % CD69 1 μg/ml DN3 |
|---|---|---|---|---|
| 66 and 74 | 5'-TCG₁TCG₁TT-XXX-*GUCUCGAGAC*-5' | 8.1 | 8.3 | 11.4 |
| 66 and 75 | 5'-TCG₁TCG₁TT-XXX-GTCTCCACTC-5' | 38.9 | 25.7 | 33.3 |
| 66 and 76 | 5'-TCG₁TCG₁TT-XXX-*GUCUCCACUC*-5' | 10.8 | 28.9 | 12.5 |
| 66 and 47 | 5'-TCG₁TCG₁TT-XXX-GTCTCGAGAC-5' | 28.6 | 40 | 9.5 |
| 66 and 72 | 5'-TCG₁TCG₁TT-XXX-*GUCUCGAGAC*-5' | 8.4 | 24 | 7.3 |
| Media | | 5.9 | 11.5 | 7.6 |

| SEQ ID NO | Sequences and Modification (5'-3') | % CD69 1 μg/ml DN4 | % CD69 1 μg/ml DN5 | % CD69 1 μg/ml DN6 |
|---|---|---|---|---|
| 66 and 74 | 5'-TCG₁TCG₁TT-XXX-*GUCUCGAGAC*-5' | 6.1 | 11.9 | 10.5 |
| 66 and 75 | 5'-TCG₁TCG₁TT-XXX-GTCTCCACTC-5' | 11.4 | 20 | 19.5 |
| 66 and 76 | 5'-TCG₁TCG₁TT-XXX-*GUCUCCACUC*-5' | 12.5 | 9.3 | 15 |
| 66 and 47 | 5'-TCG₁TCG₁TT-XXX-GTCTCGAGAC-5' | 14.8 | 20.5 | 21.4 |

TABLE 8-continued

Immunomer Structure and Expression of BC from Human PBMC (24 hs)

| | | | | |
|---|---|---|---|---|
| 66 and 72 | 5'-TCG₁TCG₁TT-XXX-<u>GUCUCGAGAC</u>-5' | 6.1 | 11.7 | 14.6 |
| Media | | 5.4 | 10.2 | 11.1 |

Normal phase represents a phosphorothioate linkage; Italic phase represents a phosphodiester linkage; Underline = 2'-OMe-nucleoside; R = 2'-deoxy-7-deazaguanosine G₁ = 2'-deoxy-7-deazaguanoise; X-Glycerol linker

TABLE 9

Immunomer Structure and Expression of DC from Human PBMC (24 hs)

| SEQ ID NO | Sequences and Modification (5'-3') | % CD86 1 μg/mL DN1 | % CD86 1 μg/mL DN2 | % CD86 1 μg/mL DN3 |
|---|---|---|---|---|
| 64 and 71 | 5'-TCRTCRTT-X-GTGAGCTCTGT-G\\<br>\|\|\|\|\|\|\|\|\|\|\|  A<br>3'-CACTCGAGACA-A/ | 39.1 | 34.5 | 31.9 |
| 65 | 5'-TCRTCRTT-GTGAGCTCTGT-G\\<br>\|\|\|\|\|\|\|\|\|\|\|  A<br>3'-<u>CACUCGAGACA</u>-A/ | 27.3 | 17.7 | 29 |
| 64 and 73 | 5'-TCRTCRTT-X-<u>GUGAGCUCUGU</u>-G\\<br>\|\|\|\|\|\|\|\|\|\|\|  A<br>3'-<u>CACUCGAGACA</u>-A/ | 20.4 | 6.9 | 26.7 |
| Media | | 6.6 | 1.5 | 16.2 |

| SEQ ID NO | Sequences and Modification (5'-3') | % CD86 1 μg/mL DN4 | % CD86 1 μg/mL DN5 | % CD86 1 μg/mL DN6 |
|---|---|---|---|---|
| 64 and 71 | 5'-TCRTCRTT-X-GTGAGCTCTGT-G\\<br>\|\|\|\|\|\|\|\|\|\|\|  A<br>3'-CACTCGAGACA-A/ | 23.8 | 23.2 | 26.8 |
| 65 | 5'-TCRTCRTT-GTGAGCTCTGT-G\\<br>\|\|\|\|\|\|\|\|\|\|\|  A<br>3'-<u>CACCUCGAGACA</u>-A/ | 18 | 30.1 | 22.8 |
| 64 and 73 | 5'-TCRTCRTT-X-<u>GUGAGCUCUGU</u>-G\\<br>\|\|\|\|\|\|\|\|\|\|\|  A<br>3'-<u>CACTCGAGACA</u>-A/ | 15.1 | 9.1 | 15.8 |
| Media | | 15.7 | 15.2 | 7 |

Normal phase represents a phosphorothioate linkage; Underline = 2'-OMe-nucleoside; R = 2'-deoxy-7-deazaguanosine; X = C3-linker

| SEQ ID NO | Sequences and Modification (5'-3') | % CD86 1 μg/mL DN1 | % CD86 1 μg/mL DN2 | % CD86 1 μg/mL DN3 |
|---|---|---|---|---|
| 66 and 74 | 5'-TCG₁TCG₁TT-XXX-<u>*GUCUCGAGAC*</u>-5' | 24.8 | 7.9 | 13.2 |
| 66 and 75 | 5'-TCG₁TCG₁TT-XXX-GTCTCCACTC-5' | 13.1 | 14.2 | 17.4 |
| 66 and 76 | 5'-TCG₁TCG₁TT-XXX-<u>GUCUCCACUC</u>-5' | 48.7 | 35 | |
| 66 and 47 | 5'-TCG₁TCG₁TT-XXX-GTCTCGAGAC-5' | 51.3 | 45.7 | |
| 66 and 72 | 5'-TCG₁TCG₁TT-XXX-<u>GUCUCGAGAC</u>-5' | 48 | 31.5 | |
| Media | | 6.6 | 1.5 | 15.7 |

TABLE 9-continued

Immunomer Structure and Expression of DC from Human PBMC (24 hs)

| SEQ ID NO | Sequences and Modification (5'-3') | % CD86 1 µg/mL DN4 | % CD86 1 µg/mL DN5 | % CD86 1 µg/mL DN6 |
|---|---|---|---|---|
| 66 and 74 | 5'-TCG$_1$TCG$_1$TT-XXX-*GUCUCGAGAC*-5' | 6.9 | 10.1 | 12.6 |
| 66 and 75 | 5'-TCG$_1$TCG$_1$TT-XXX-GTCTCCACTC-5' | 37.5 | 42.5 | 30.5 |
| 66 and 76 | 5'-TCG$_1$TCG$_1$TT-XXX-*GUCUCCACUC*-5' | 23 | 31.3 | 13.5 |
| 66 and 47 | 5'-TCG$_1$TCG$_1$TT-XXX-GTCTCGAGAC-5' | 42.8 | 45 | 27.6 |
| 66 and 72 | | 9.1 | 7 | 7.4 |

Normal phase represents a phosphorothioate linkage; Italic phase represents a phosphodiester linkage.
Underline = 2'-OMe-nucleoside
R = 2'-deoxy-7-deazaguanosine G$_1$ = 2'-deoxy-7-deazaguanoise
X = Glycerol linker

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A method for treating cancer, infection, inflammatory disease or autoimmune disease comprising administering to a patient an immunostimulatory nucleic acid, having secondary structure formed by intermolecular hydrogen bonding between two oligonucleotide compounds, wherein each of the oligonucleotide compounds comprise the general structure of:

$$\text{Domain A-Domain B-Domain C,} \qquad (I)$$

wherein Domain A is 5'-3' DNA not having a palindromic or self-complementary domain and containing at least one dinucleotide selected from the group consisting of CpG, C*pG, C*pG* and CpG*, wherein C is cytidine or 2'-deoxycitidine, G is guanosine or 2'-deoxyguanosine, C* is 2'-deoxythymidine, 1-(2'-deoxy-β-D-ribofuranosyl)-2-oxo-7-deaza-8-methyl-purine, 2' dideoxy-5-halocytosine, 2'-dideoxy-5-nitrocytosine, arabinocytidine, 2'-deoxy-2'-substitutedarabinocytidine, 2'-O-substituted arabinocytidine, 2'-deoxy-5-hydroxycytidine, 2'-deoxy-N4-alkyl-cytidine, 2'-deoxy-4-thiouridine, or other non-natural pyrimidine nucleosides, G* is 2' deoxy-7-deazaguanosine, 2'-deoxy-6-thioguanosine, arabinoguanosine, 2'-deoxy-2'-substituted-arabinoguanosine, 2'-O-substituted-arabinoguanosine, 2'-deoxyinosine, or other non-natural purine nucleoside, and p is an internucleoside linkage selected from the group consisting of phosphodiester, phosphorothioate, and phosphorodithioate, wherein Domain B is a non-nucleoside linker joining Domain A and Domain C, wherein Domain C is 3'-5' DNA or RNA having a palindromic or self-complementary domain allowing for intermolecular hydrogen bonding, and which can or cannot have a dinucleotide selected from the group consisting of CpG, C*pG, C*pG* and CpG*, wherein C is cytidine or 2'deoxycitidine, G is guanosine or 2' deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other non-natural pyrimidine nucleosides, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside, p is an internucleoside linkage selected from the group consisting of phosphodiester and phosphorothioate, and wherein each oligonucleotide compound comprises from about 12 to about 50 nucleotides in length.

2. The method according to claim 1, wherein Domain A contains at least one dinucleotide selected from the group consisting of C*pG, C*pG* and CpG*.

3. The method according to claim 1, wherein Domain C contains at least one dinucleotide selected from the group consisting of CpG, C*pG, C*pG* and CpG*.

4. The method according to claim 1, wherein each oligonucleotide compound comprises from about 12 to about 26 nucleotides in length.

5. The method according to claim 1, wherein the immunostimulatory nucleic acid has the structure:

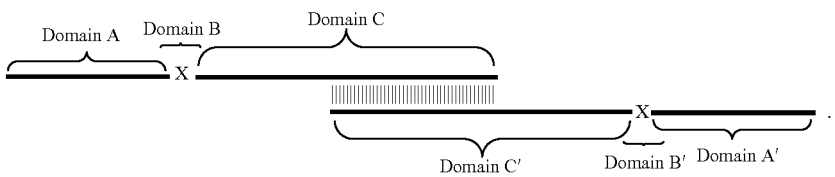

6. A method for treating cancer, infection, inflammatory disease or autoimmune disease comprising administering to a patient an immunostimulatory nucleic acid, having secondary structure formed by intermolecular hydrogen bonding between at least two oligonucleotide compounds, wherein each of the oligonucleotide compounds comprise the general structure of:

$$\text{Domain A-Domain B-Domain C,} \qquad (I)$$

wherein Domain A is 5'-3' DNA having a palindromic or self-complementary domain allowing for intermolecular hydrogen bonding and containing or not containing at least one dinucleotide selected from the group consisting of CpG, C*pG, C*pG* and CpG*, wherein C is cytidine or 2'-deoxycitidine, G is guanosine or 2'-deoxyguanosine, C* is 2'-deoxythymidine, 1-(2'-deoxy-β-D-ribofuranosyl)-2-oxo-7-deaza-8-methyl-purine, 2' dideoxy-5-halocytosine, 2'-dideoxy-5-nitrocytosine, arabinocytidine, 2'-deoxy-2'-substitutedarabinocytidine, 2'-O-substituted arabinocytidine, 2'-deoxy-5-hydroxycytidine, 2'-deoxy-N4-alkyl-cytidine, 2'-deoxy-4-thiouridine, or other non-natural pyrimidine nucleosides, G*is 2' deoxy-7-deazaguanosine, 2'-deoxy-6-thioguanosine, arabinoguanosine, 2'-deoxy-2'-substituted-arabinoguanosine, 2'-O-substituted-arabinoguanosine, 2'-deoxyinosine, or other non-natural purine nucleoside, and p is an internucleoside linkage selected from the group consisting of phosphodiester, phosphorothioate, and phosphorodithioate, wherein Domain B is a-non-nucleoside linker joining Domain A and Domain C, wherein Domain C is 3'-5' DNA or RNA having a palindromic or self-complementary domain allowing for intermolecular hydrogen bonding and containing or not containing at least one dinucleotide selected from the group consisting of CpG, C*pG, C*pG* and CpG*, wherein C is cytidine or 2'deoxycitidine, G is guanosine or 2' deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other non-natural pyrimidine nucleosides, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside, p is an internucleoside linkage selected from the group consisting of phosphodiester and phosphorothioate; provided that Domain A or Domain C has at least one dinucleotide selected from the group consisting of CpG, C*pG, C*pG* and CpG*, and wherein each oligonucleotide compound comprises from about 12 to about 50 nucleotides in length.

7. The method according to claim 6, wherein each oligonucleotide compound comprises from about 12 to about 26 nucleotides.

8. The method according to claim 6, wherein the immunostimulatory nucleic acid has the structure:

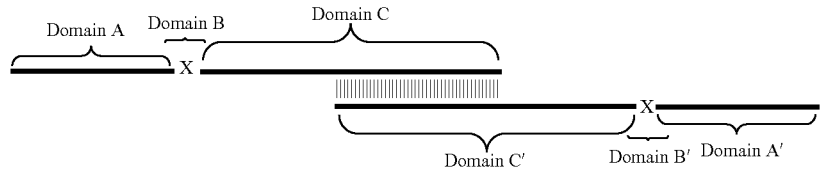

9. The method according to claim 6, wherein Domain A contains at least one dinucleotide selected from the group consisting of CpG, C*pG, C*pG* and CpG*.

10. The method according to claim 6, wherein Domain C contains at least one dinucleotide selected from the group consisting of CpG, C*pG, C*pG* and CpG*.

11. The method according to claim 6, wherein Domain A and Domain C contain at least one dinucleotide selected from the group consisting of CpG, C*pG, C*pG* and CpG*.

12. The method according to claim 1, wherein the infection is a viral infection.

13. The method according to claim 1, wherein the infection is a bacterial infection.

14. The method according to claim 1, wherein the inflammatory disease is asthma.

15. The method according to claim 1, wherein the inflammatory disease is allergy.

16. The method according to claim 1, further comprising administering a vaccine, antigen or an antisense oligonucleotide.

17. Then method according to claim 16, wherein the vaccine is a cancer vaccine.

18. The method according to claim 17, wherein the cancer vaccine is selected from the group consisting of EFG, Anti-idiotypic cancer vaccines, Gp75 antigen, GMK melanoma vaccine, MGV ganglioside conjugate vaccine, Her2/new, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-vased vaccine, PACIS, BCG vaccine, TA-HPV, TA-CIN, DISC-virus and ImmunCyst/TheraCys.

19. The method according to claim 6, wherein the infection is a viral infection.

20. The method according to claim 6, wherein the infection is a bacterial infection.

21. The method according to claim 6, wherein the inflammatory disease is asthma.

22. The method according to claim 6, wherein the inflammatory disease is allergy.

23. The method according to claim 6, further comprising administering a vaccine, antigen or an antisense oligonucleotide.

24. Then method according to claim 23, wherein the vaccine is a cancer vaccine.

25. The method according to claim 24, wherein the cancer vaccine is selected from the group consisting of EFG, Anti-idiotypic cancer vaccines, Gp75 antigen, GMK melanoma vaccine, MGV ganglioside conjugate vaccine, Her2/new, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-vased vaccine, PACIS, BCG vaccine, TA-HPV, TA-CIN, DISC-virus and ImmunCyst/TheraCys.

* * * * *